US008224582B2

(12) United States Patent
Krylov et al.

(10) Patent No.: US 8,224,582 B2
(45) Date of Patent: Jul. 17, 2012

(54) NON-EQUILIBRIUM CAPILLARY ELECTROPHORESIS OF EQUILIBRIUM MIXTURES (NECEEM)-BASED METHODS FOR DRUG AND DIAGNOSTIC DEVELOPMENT

(75) Inventors: Sergey N. Krylov, Toronto (CA);
Svetlana M. Krylova, Toronto (CA);
Maxim Berezoski, Toronto (CA)

(73) Assignees: Sergery Krylov, Toronto (CA);
Svetlana Krylova, Toronto (CA)

( * ) Notice: Subject to any disclaimer, the term of this patent is extended or adjusted under 35 U.S.C. 154(b) by 276 days.

(21) Appl. No.: 12/685,728

(22) Filed: Jan. 12, 2010

(65) Prior Publication Data
US 2010/0243450 A1    Sep. 30, 2010

Related U.S. Application Data

(62) Division of application No. 10/610,547, filed on Jul. 2, 2003, now Pat. No. 7,672,786.

(51) Int. Cl.
*G01N 33/50* (2006.01)
*G01N 33/48* (2006.01)

(52) U.S. Cl. ............................................. 702/19; 702/20

(58) Field of Classification Search ........................ None
See application file for complete search history.

(56) References Cited

U.S. PATENT DOCUMENTS
6,299,747 B1    10/2001    Dunayevskiy et al.

FOREIGN PATENT DOCUMENTS
| | | |
|---|---|---|
| WO | WO97/22000 | 6/1997 |
| WO | WO99/34203 | 7/1999 |
| WO | WO00/03240 | 1/2000 |
| WO | WO00/79260 A1 | 12/2000 |
| WO | WO03/102212 | 12/2003 |

OTHER PUBLICATIONS

Berezovski, M et al., "Affinity Analysis of a Protein—Aptamer Complex Using Nonequilibirum Capillary Electophoresis of Equilibrium Mixtures", Anal. Chem. 2003, 75, 1382-1386.
Okhonin, V. et al., "Nonequilibirum Capillary Electophoresis of Equilibrium Mixtures, Mathematical Model", Anal. Chem. 2004, 76, 1507-1512.
Berezovski, M. et al., "Using nonequilibirum Capillary Electophoresis of Equilibirum Mixtures for the Determination of Temperature in Capillary Electrophoresis", Anal. Chem. 2004, 76, 7114-7117.
Berezovski, M. et al., "Theromchemisty of Protein—DNA Interaction Studied with Temperature-Controlled Nonequilibrium Capillary Electorphoresis of Equilibrium Mixtures", Anal. Chem. 2005, 77, 1526-1529.
Drabovick, A. et al., "Selection of smart Aptamers by Methods of Kinetic Capillary Electrophoresis", Anal. Chem, 2006, 78, 3171-3178.
Okhonin, V. et al., "Plug-Plug Kinetic Capillary Electrophoresis: Method for Direct Determination of Rate Constants of Complex Formation and Dissociation", Anal. Chem. 2006, 78, 4803-4810.
Drabovich, A. et al., "Selection of Smart Small-Molecule Ligands: The Proof of Principle", Anal. Chem. 2009, 81, 490-494.
Yunusov, D. et al., "Kinectic capillary electrophrosis-based affinity screening of aptamer clones", Analyticia Chimica Acta 631, 2009, 102-107.
Krylov, S., "Kinetic CE: Foundation for homogeneous kinetic affinity methods" Electrophoresis 2007, 28, 69-88.
Berezovski, M. et al., "Nonequilibirum Capillary Electrophoresis of Equilibrium Mixtures: A Universal Tool for Development of Aptamers" J. AM. Chem. Soc., 2005, 127, 3165-3171.
Petrov, A. et al., "Kinectic Capillary Electrophoresis (KCE): A Conceptual Platform for Kinectic Homeogeneous Affinity Methods", J. Am. Chem. Soc. 2005, 127, 17104-17110.
Berexovski, M. et al., "Non-Selex Selection of Aptamers", J. Am. Chem. Soc. 2006, 128, 1410-1411.
Drabovich, A. et al., "Smart Aptamers Facilitate Multi-Probe Affinity Analysis of Proteins with Ultra-Wide Dynamic Range of Measured Concentrations", J. Am. Chem. Soc, 2007, 129, 7260-7261.
Krylov, S., "Non-equilibirum Capillary Electrophoresis of Equilibrium Mixtures (NECEEM): A Novel Method for Biomolecular Screening", Society for Biomolecular Sciences, 2006, 115-122.
Krylov, S., "NECEEM for development, characterisation and analytical utilisation of apatmers", LabPlus International, Nov. 2005.
Javaherian, S. et al., "Selection of aptamers for a protein target in cell lysate and their application to protein purificaiton", Nucleic Acids Research, 2009, vol. 37 No. 8.
Berzovski, M. et al., "Non-Selex: selection of aptamers without intermediate amplication of candidate oligonucleotides", Nature Protocols, vol. 1, No. 3, 2006, 1359-1369.
Imanishi M., and Sugiura Y., Artificial DNA-Bending Six-Zinc Finger Peptides with Different Charged Linkers: District Kinetic Properties of DNA Bindings, Biochemistry, 2002, 41, 1328.
Wan Q.-H., and Le X. C., Studies of Protein-DNA Interactions by Capillary Electrophoresis/Laser-Induced Fluorescence Polarization, Anal. Chem., 2000, 72, 5583.

(Continued)

Primary Examiner — Jason Sims
(74) Attorney, Agent, or Firm — Bereskin & Parr LLP/S.E.N.C.R.L., s.r.l.; Patricia Folkins

(57) ABSTRACT

The invention discloses a Non-Equilibrium Capillary Electrophoresis of Equilibrium Mixtures (NECEEM) method and NECEEM-based practical applications. The NECEEM method is a homogeneous technique, which, in contrast to heterogeneous methods, does not require affixing molecules to a solid substrate. The method of the invention facilitates 3 practical applications. In the first application, the method allows the finding of kinetic and thermodynamic parameters of complex formation. It advantageously allows for revealing two parameters, the equilibrium dissociation constant, $K_d$, and the monomolecular rate constant of complex decay, $k_{off}$, in a single experiment. In the second practical application, the method of this invention provides an approach for quantitative affinity analysis of target molecules. It advantageously allows for the use of affinity probes with relatively high values of $k_{off}$. In the third practical application, the method of this invention presents a new and powerful approach to select target-binding molecules (ligands) from complex mixtures.

18 Claims, 16 Drawing Sheets

OTHER PUBLICATIONS

Le X. C., Wan Q. H., Lam M. T., Fluorescence polarization detection for affinity capillary electrophoresis, Electrophoresis, 2002, 23, 903.

Chu Y,-H., Cheng C. C., Affinity capillary electrophoresis in biomolecular recognition . Cell. and Mol. Life Sci., 1998, 54, 663.

Anderson J. R. et al., Analysis by Capillary Electrophoresis of the Kinetics of Charge Ladder Formation for Bovine Carbonic Anhydrase. Anal. Chem., 2002, 74, 1870.

Tim et al., Uttratrace analysis of drugs in biological fluids using affinity probe capillary electrophoresis: Analysis of dorzolamide with fluorescently labeled carbonic adhydrase, Electrophoresis, 2000, 21, 220.

Heegaard Niels H. H. et al. Identification, quantitarion, and characterization of biomolecules by capillary electrophoretic analysis of binding interactions.

German et al., Aptamers as Ligands in Affinity Probe Capillary Electrophoresis, Anal. Chem., 1998, 70, 4540.

Simon R. J., Zuckermann et al., Peptoids: A Modular Approach to Drug Discovery, Proc. Natl. Acad. Sci. U.S.A. 1992, 89, 4605.

Fodor et al., Light-Directed, Spatially Addressable Parallel Chemical Synthesis, Science, 1991, 251, 787.

Whitelegge et al., Proteomics: Making sense of genomic information for drug discovery, Am. J. PharmacoGenomics, 2001, 1, Abstract.

Yao et al., Inhibition-Based Metabolic Drug-Drug Interactions: Predictions from In Vitro Data J. Pharm. Sci., 2002, 91, 1923.

Roberts, S.A., High-Throughput screening approaches for investigating drug metabolism and pharmacokinetics, Xenobiotica, 2001, 31, 557.

Schuck P., Reliable determination of binding affinity and kinetics using surface plasmon resonance biosensors, Curr. Opin. Biotechnol, 1997, 8, 498.

White R. J., Phillips D. R., Transcriptional Analysis of Multisite Drug-DNA Dissociation Kinetics: Delayed Termination of Transcription by Actinomycin D, et al., Biochemistry, 1988, 27, 91222.

Busch M.H.A.et al., Comparison of five methods for the study of drug-protein binding in affinity capillary electrophoresis, Electrophoresis, 1999, 20, 3122.

Galbusera, C. et al., Molecular interaction in capillary electrophoresis, Current Opinion in Biotechnology, 2003, 14, 126.

Mendosa, S.D. et al., In vitro evolution of functional DNA using capillary electrophoresis, 2004, 126, 20, published on web Dec. 9, 2003.

Schematic representation of a NECEEM electropherogram during the selection of ligands with $K_d < [T]_1$ and $k_{on} > 1/[T]_1 t_{eq1}$ if the migration time of T is unknown. Ligands are collected from both sides of the peak L.
Region 1 is where L•T or L formed from the decay of L•T are collected
Region 2 is where L•T or L formed from the decay of L•T are collected

Figure 4
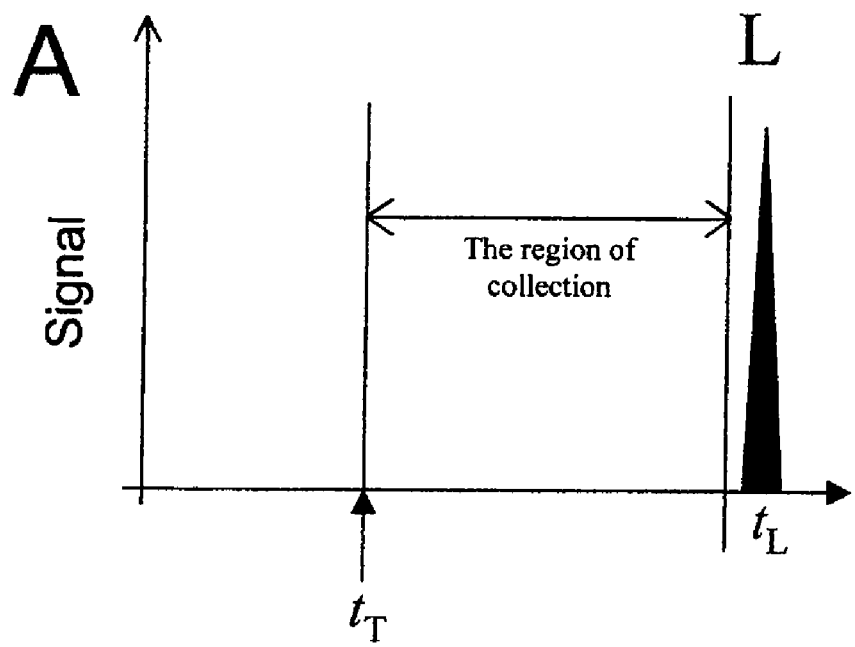
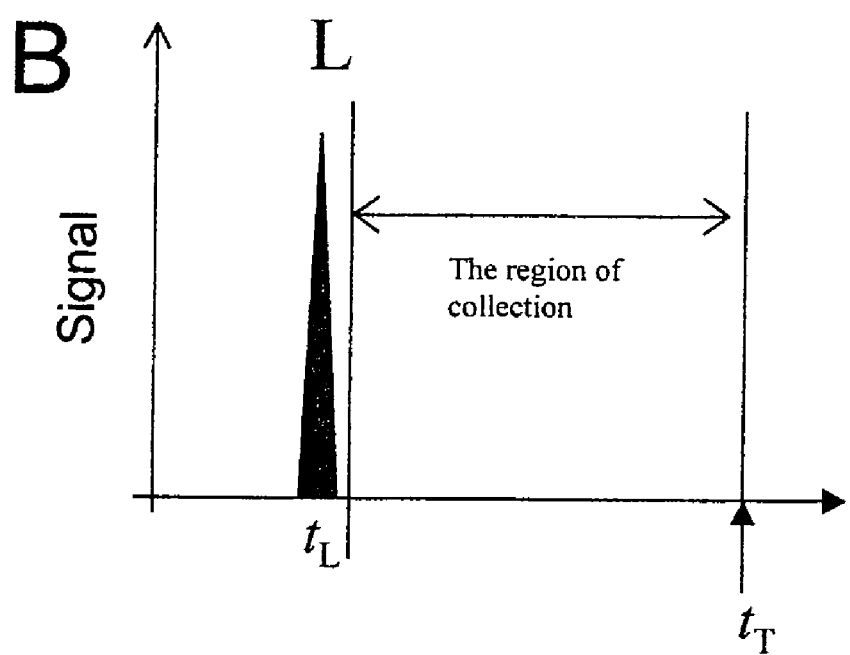

Figure 6
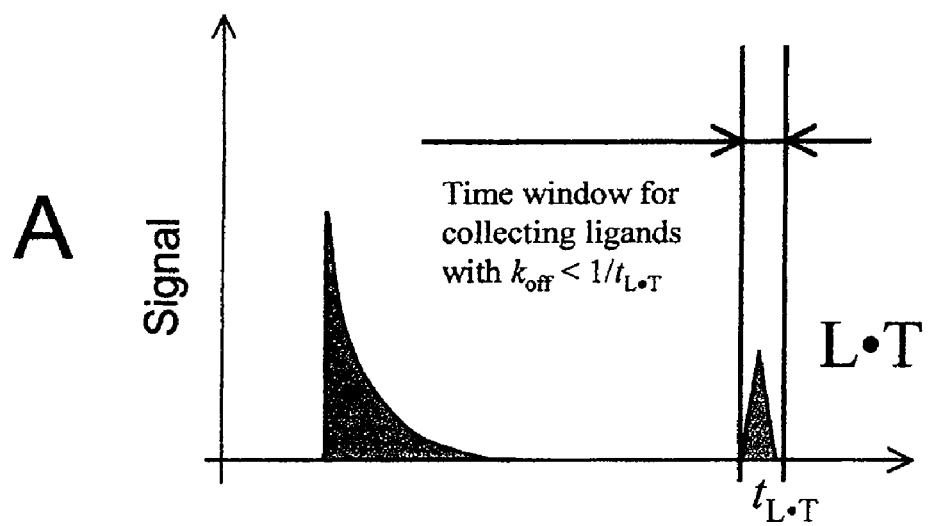
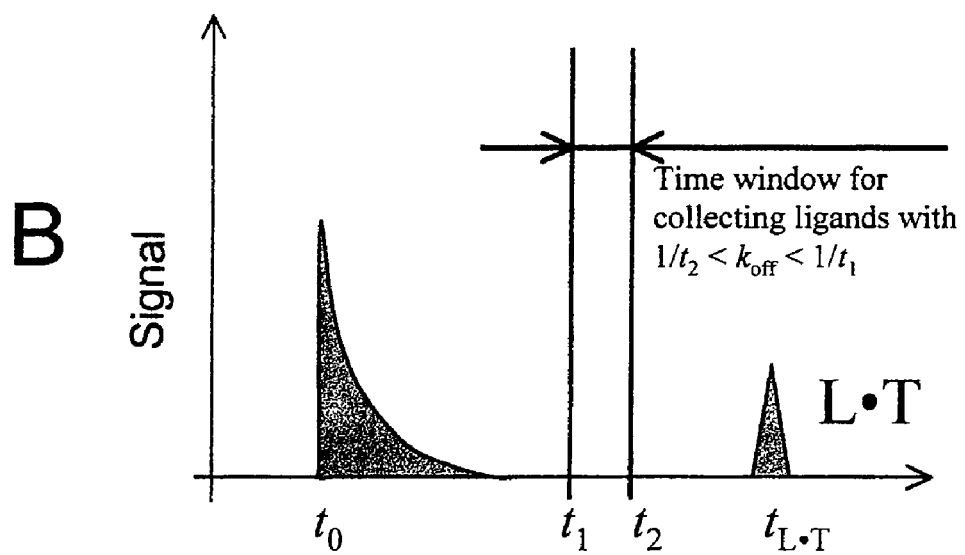

Figure 15. Selection of aptamers to farnesyltransferase from a combinatorial library of oligonucleotides.

NON-EQUILIBRIUM CAPILLARY ELECTROPHORESIS OF EQUILIBRIUM MIXTURES (NECEEM)-BASED METHODS FOR DRUG AND DIAGNOSTIC DEVELOPMENT

This application is a divisional application of U.S. application Ser. No. 10/610,547, filed Jul. 2, 2003, now U.S. Pat. No. 7,672,786, the contents of which are herein incorporated herein, in their entirety, by reference.

INCORPORATION OF SEQUENCE LISTING

A computer readable form of the Sequence Listing "13502-6_Sequence_Listing.txt" (1,811 bytes), submitted via EFS-WEB and created on Jun. 14, 2010, is herein incorporated by reference.

FIELD OF THE INVENTION

The invention relates to the field of non-equilibrium capillary electrophoresis of equilibrium mixtures and the use of the method, particularly in the development of drugs, treatment regimes and diagnostic methods.

BACKGROUND OF THE INVENTION

Non-covalent molecular complexes play a crucial role in regulatory biological processes, such as, but not limited to gene expression, DNA replication, signal transduction, cell-to-cell interaction, and the immune response. The molecular mechanisms of action of many drugs are based on drugs forming non-covalent molecular complexes with therapeutic targets. In addition, the formation of non-covalent molecular complexes is pivotal to many analytical techniques and devices used in research and disease diagnostics, such as, but not necessarily limited to, immunoassays, biosensors, and DNA hybridization analyses (Cepek and Brenner, *Nature* 1994, 372, 190; Sparks et al. *Med. Chem.* 1993, 36; Cohen and Williams, *Microbiol. Sci.* 1988, 5, 265; Pantoliano and Horlick, *Biochemistry* 1994, 33, 10229; Karlsson, *Trends Pharm. Sci.* 1991, 12, 265; Dalgleish and Kennedy, *Vaccine* 1988, 6, 215; Christian et al. *Biochem. J.* 1994, 300, 165).

The formation and decay of a non-covalent complex, L•T, between molecules L (ligand) and T (target), are characterized by a bimolecular rate constant $k_{on}$, and a monomolecular rate constant, $k_{off}$, respectively:

$$L + T \underset{k_{off}}{\overset{k_{on}}{\rightleftharpoons}} L \cdot T \quad (1)$$

where $k_{on}$ is the rate constant of the forward reaction forming L•T and $k_{off}$ is the rate constant of the reverse reaction. The stability of the complex is often described in terms of the equilibrium dissociation constant:

$$K_d = k_{off}/k_{on} \quad (2)$$

The three constants, $k_{on}$, $k_{off}$, and $K_d$, are interconnected through equation 2, therefore defining any pair of constants will define the third. The constants are also dependent on a number of parameters, such as but not limited to buffer composition, buffer pH, buffer ionic strength, and temperature.

Determination of $k_{on}$, $k_{off}$ and $K_d$. Knowledge of $k_{on}$, $k_{off}$, $K_d$, and their dependence on certain factors such as buffer composition, buffer pH, buffer ionic strength, and temperature can assist in: (i) understanding the dynamics of biological processes, (ii) determining the pharmacokinetics of target-binding drugs, and (iii) the designing of quantitative affinity analyses. In practical terms the determination of $k_{on}$, $k_{off}$, $K_d$ can assist in developing and/or selecting drugs with desired kinetic parameters. It may also help in developing suitable dosage regimes. In another aspect it can help in the development of screening and/or diagnostic assays.

Prior art methods for measuring $k_{on}$, $k_{off}$ and $K_d$ of a molecular interaction have significant limitations. The methods that are used for finding $k_{on}$ and $k_{off}$ can be divided into two broad categories: heterogeneous and homogeneous binding assays. In heterogeneous assays, T is affixed to a solid substrate, while L is dissolved in a solution and can bind T affixed to the surface. In advanced heterogeneous binding assays such as surface plasmon resonance (SPR), T is affixed to a sensor that can change its optical or electrical signal upon L binding to T (Imanishi and Sugiura, *Biochemistry*, 2002, 41, 1328; Cheskis and Freedman, *Biochemistry*, 1996, 35, 3309). In such methods, $K_d$ can be found by performing a series of equilibrium experiments. The concentration of L in the solution is varied and the interaction between L and T is allowed to reach equilibrium. The signal from the sensor versus the concentration of L has a characteristic sigmoidal shape and $K_d$ can be found from the curve by identifying the concentration of L at which the signal is equal to half of its maximum amplitude. The $k_{off}$ value can be determined by SPR in a single non-equilibrium experiment in which the equilibrium is disturbed by fast replacing the solution of L with a buffer devoid of L. The complex on the surface decays in the absence of L in the solution, and the complex decay generates an exponential signal on the sensor.

Heterogeneous binding assays have certain advantages and drawbacks. The most serious drawback is that affixing T to the surface changes the structure of T. The extent of such change will depend on the method of immobilization. The change in the structure can potentially affect the binding parameters of L to T. This problem is especially severe for L that binds to T through interaction with a large part of T. In addition, the immobilization of T on the surface may be time-consuming and expensive. Moreover, non-specific interactions with the surface are always a concern.

In homogeneous binding assays T and L are mixed and allowed to form a complex in solution; neither of the molecules are affixed to the surface. Complex formation is followed by either monitoring the changing physical-chemical properties of L or T upon binding. Such properties can be optical (absorption, fluorescence, polarization) or separation-related (chromatographic or electrophoretic mobility). Equilibrium experiments with varying concentrations of L can be used similarly to heterogeneous analyses to find $K_d$. Non-equilibrium stopped flow-experiments, in which L and T are mixed in a fast fashion and the change in spectral properties is monitored, can be used to find $k_{on}$. Non-equilibrium chromatographic experiments, in which a competitive ligand is added to the chromatographic buffer and allowed to interact with T was demonstrated to be useful in finding $K_d$ and $k_{off}$, although the method involved "non-transparent" numerical analysis of chromatographic peaks and required an additional reactant, the competitive ligand.

When the quantity of available T or L is a limiting factor, capillary electrophoresis (CE) is the method of choice. It requires only nanoliter (nL) volumes of a sample and can detect fewer than 1000 molecules (Wu and Dovichi *J. Chromatogr.* 1989, 480, 141). Affinity capillary electrophoresis (ACE), in which L is added to the run buffer at different concentrations and the change of the mobility of T is monitored, can be used to determine $K_d$ by conducting a series of equilibrium experiments (Wan and Le, *Anal. Chem.*, 2000, 72, 5583; Le et al., *Electrophoresis*, 2002, 23, 903; Chu et al. *J. Med. Chem.*, 1992, 35, 2915; Chu and Whitesides, *J. Org. Chem.* 1992, 57, 3524; Carpenter et al. *J. Chem. Soc., Chem. Commun.* 1992. 804; Chu et al. *Cell. and Mol. Life Sci.*, 1998, 54, 663). However, ACE is an equilibrium approach that cannot be used for finding $k_{off}$.

Quantitative affinity analyses. Equilibrium binding analyses described in the previous section can be converted into methods for the quantitative analysis of T using the affinity probe L. Three major categories of affinity probes include antibodies (used in immunoassays), DNA hybridization probes (used in analyses of DNA and RNA) (Pease et al. *P. Natl. Acad. Sci. USA* 1994, 91, 5022; Mullaart et al. *Nature*, 1993, 365, 469; Higuchi et al. *Nature*, 1988, 332, 543), and aptamers (synthetic affinity probes, e.g. oligonucleotides or oligopeptides) (Clark and Remcho, *Electrophoresis* 2002, 23, 1335; Li et al. *Biochem. Biophys. Res. Commun.*, 2002, 292, 31; Fredriksson et al. *Nat. Biotechnol.*, 2002, 20, 473). When a target is available in very low amounts and cannot be amplified (i.e. not subject to PCR), CE can be the method of choice for developing a quantitative affinity analysis (Colton et al. *Electrophoresis*, 1998, 19, 367; Anderson et al. *Anal. Chem.*, 2002, 74, 1870; Tim et al., *Electrophoresis*, 2000, 21, 220; Heegaard et al., *Electrophoresis*, 1999, 20, 3122; Busch et al., *J. Chromatography A*, 1997, 777, 311). In CE-based quantitative analyses the mobility shift of the affinity probe, L, is measured upon binding to the target, T. The shift is a function of the concentration of T. One of the major limitations of CE is its poor performance for antibodies as affinity probes. High molecular weight of antibodies significantly limits the mobility shift upon binding to a usually smaller target molecule. Recent advances in developing oligonucleotide aptamers open the possibility of their use as affinity probes in CE-based analyses (German et al. *Anal. Chem.*, 1998, 70, 4540). Such analyses have been demonstrated in ACE mode, where the target is added to the buffer. However, ACE has two drawbacks for quantitative affinity analyses. If the target is a protein, its addition to the separation buffer is typically associated with protein adsorption to capillary walls, which can severely affect the quality of analysis (Gomez et al., *Anal. Chemistry*, 1994, 66, 1785). Second, adding the target to the running buffer can be unacceptable if the amount of target available is very small. An alternative to the ACE analysis is: (i) forming the L•T complex out of the capillary and injecting a small plug of the mixture into the capillary, (ii) separating free L from the L•T complex using a buffer free of T and L, and (iii) monitoring peaks corresponding to L and L•T. However, this method is not applicable to L•T complexes with relatively high values of $k_{off}$ ($>10^{-2}$ s$^{-1}$) since the complex considerably decays during the separation (the typical separation time is ~1000 s), which affects the accuracy of measurements. Many aptamers available today, especially those for small-molecule targets, have $k_{off}$ values that do not allow for their use as affinity probes in such CE-based analyses.

Screening for and selecting drug candidates and affinity probes. Finding new molecules capable of binding to therapeutic targets is essential for both drug discovery and development of new diagnostic methods. Target-binding molecules are used as potential drug candidates and as affinity probes for detecting targets. One of the most efficient ways of finding new target-binding molecules is the screening of complex biological (e.g. extracts from animal and plant tissues) and synthetic (e.g. combinatorial libraries of compounds) mixtures in binding assays (Chu et al., *J. Org. Chem.*, 1993, 58, 648; Kuntz, *Science* 1992, 257, 1078; Baumbach et al., *BioPhrm* 1992, 5, 24; Pauwels et al., *Nature*, 1990, 343, 470; Sandler and Smith, *Design of Enzyme Inhibitors as Drugs*, 1989; Zuckermann et al., *Proc. Natl. Acad. Sci. U.S.A.* 1992, 89, 4605; Fodor et al., *Science*, 1991, 251, 787; Lam et al., *Nature* 1991, 354, 81; Whitelegge et al., *Am. J. Pharm. Genomics*, 2001, 1, 29; Yao et al., *J. Pharm. Sci.*, 2002, 91, 1923; Fortin and Nolan, *Chemistry & Biology*, 2002, 9, 670; Siegel, *Current Topics in Medicinal Chemistry*, 2002, 2, 13; Roberts, *Xenobiotica*, 2001, 31, 557; Gold, *Nat. Biotechnol.* 2002, 20, 671). Hereafter, the mixture to be screened will be called the sample.

Methods used to screen samples for target-binding molecules (screening methods) also fall into two broad categories: heterogeneous and homogeneous methods. In heterogeneous methods a target is affixed to a solid substrate such as, but not limited to, chromatographic support, beads, filters, walls of microtiter plates, or SPR sensor. The target can be affixed to the surface in a number of ways. The target can be chemically immobilized onto the surface or the target can be captured by anti-target antibodies, which are bound to the surface of the solid substrate. Also, if the target is a membrane protein, the target can be affixed to the surface indirectly through cells, which adhere to the surface. In heterogeneous analyses, the sample is incubated with the target. Molecules that bind to the target are captured on the surface. The non-bound components of the sample are washed out and the target-binding molecules can then be desorbed and analyzed. Heterogeneous screening methods have a number of drawbacks typical of heterogeneous analyses in general. The most serious is that affixing the target to the surface changes the structure of the target. The extent of such change will depend on the method of immobilization. The change in the structure can potentially affect binding of molecules to the target. This problem is especially severe when target-binding molecules recognize the structure of a large part of the target. In addition, the immobilization of the target on the surface may be time-consuming and expensive. Furthermore, non-specific binding to the surface leads to the "contamination" of ligands with non-ligands. In addition all existing heterogeneous screening methods share a very serious limitation. They do not provide a means of screening for target-binding molecules with specified ranges of binding parameters: $k_{on}$, $k_{off}$ and $K_d$. Optimum binding parameters will change from application to application. For example, the $k_{on}$ and $k_{off}$ values of a drug will influence its pharmacokinetics. Depending on the mechanism of a drug's action, the mechanism of its side effects, and the desirable regime of its administration, different binding parameters will be optimal (Bruice and Kahn, *Curr. Opin. Chem. Biol.*, 2000, 4, 540; Van Oss, *J. Mol. Recogn.*, 1997, 10, 203; Schuck, *Curr. Opin. Biotechnol*, 1997, 8, 498; White et al., *Biochemistry*, 1988, 27, 91222; Paton and Rang, *Adv. Drug. Res.* 1966, 3, 57). Different binding parameters can also be optimal for ligands to be used as affinity probes in different analyses. For example, in separation-based affinity analyses, it is desirable that $k_{off}$ be low to minimize complex decay during separation (German et al. *Anal. Chem.* 1998, 70, 4540; Berezovski and Krylov, *Anal. Chem.* 2003, 75, 1382). In fast clinical analyses, in contrast, it is essential that $k_{on}$ values be high to facilitate fast complex formation (Van Regenmortel et al., *Immunological Investigations*, 1997, 26, 67; Krishnan et al., *Env. Health Perspectives*, 1994, 102). Other types of analyses may require specific ranges of $K_d$. Thus, it would be very beneficial to have a means of selecting molecules with desirable ranges of $k_{on}$, $k_{off}$ and $K_d$.

In homogeneous screening methods, the target is mixed with the sample in solution and then subjected to either electrophoresis or chromatography. The free target is separated from the target-ligand complex based on differences in their chromatographic or electrophoretic properties. The major advantage of homogeneous screening methods over heterogeneous ones, is that they screen for molecules that bind to targets with an unmodified structure.

Despite the well-known advantages of CE, only a few CE-based homogeneous screening methods are available. Patent WO 97/22000 describes the use of a CE-based homogeneous screening method to detect compounds present in natural samples that could complex with a known target, as a tool for identifying potential therapeutic or diagnostic compounds. The method monitored changes in the migration pattern of the target during electrophoresis as a sentinel of complex formation. Due to this requirement, the method is limited to detectable concentrations of target and ligand. In addition, this method is limited to detecting complexes that remain bound as they migrate past the detector. These ligands can be referred to as tight binding ligands (TBL). Moderate (MBL) and weak binding ligands (WBL) dissociate before reaching the detector and do not produce a detectable shift in the migration pattern of the target. Hence, they are not detected.

Methods using tight binding competitive ligands (TBCL) were designed to overcome this problem. U.S. Pat. No. 6,299,747 and WO 00/79260 disclose methods of detecting new therapeutic regulatory and diagnostic compounds in complex biological materials using a known competitive ligand to the target. The TBCL is added to the target/sample mixture and peak changes of the unbound target or the target associated with the TBCL are monitored alone or together. MBLs and WBLs in the sample mixture that result in an increased unbound peak or a decreased target/TBCL peak, are detected. The patent indicates that MBLs and TBLs are detectable in the picomolar (pM) to low nanomolar (nM) range. This method, however, requires that a known TBCL exist and be available, and is limited to embodiments using detectable concentrations of target since the method relies on tracking changes in the migration pattern of the target. Homogeneous methods employing CE have also been combined with analytical methods to aid in the identification of target binding ligands. WO 00/03240 describes a method where the CE technique is combined with mass spectrometry, for screening complex samples. Again this method relies on complexes that migrate stably through the CE instrument.

Furthermore attempts have been made to select ligands that bind the chosen target with a selected binding strength. WO 99/34203 provides a method for determining relative binding strengths of ligands that bind the chosen target. This permits ligands to be ranked according to their relative binding strengths, which can aid in prioritizing further analysis. This method, however, does not provide a means of obtaining real binding parameters as the terms "affinity" and "relative affinities" are used in this patent "in a general sense, and do not necessarily refer to a hit compound's "binding affinity" to a target in an equilibrium situation".

To conclude, the existing CE-based homogeneous screening methods (WO 97/22000, U.S. Pat. No. 6,299,747, WO 00/79260 and WO 00/03240) share several serious disadvantages. They all require: (i) detectable amounts of target and (ii) large amounts of ligands capable of inducing detectable shifts of the peak of target. Due to the first requirement they are unable to select ligands for targets present in small amounts and ligands with specified binding parameters. The second requirement makes it impossible to screen for ligands that constitute only a very small portion of the screened sample, such as components of a large combinatorial library where ligand representation is low. Indeed, the relative amount of ligands, which have required binding parameters in combinatorial libraries can be as low as $10^{-13}$ (Gold, J. Biol. Chem. 270, 1995, 13581) such that the target-ligand complexes will be present in undetectable amounts, and will not introduce a mobility shift to the target. Finally, the existing CE-based homogeneous screening methods do not provide a means of selecting ligands with a specified range of $k_{on}$, $k_{off}$, and $K_d$ parameters.

SUMMARY OF THE INVENTION

Introduction

The present invention provides a Non-Equilibrium Capillary Electrophoresis of Equilibrium Mixtures (NECEEM)-based method for determining and using equilibrium and/or kinetic parameters of complex formation between two components, such as of a bimolecular interaction. In a preferred embodiment, the method is a homogeneous method. In another embodiment, the method can be used to screen for selecting components of a bimolecular interaction that have specified kinetic or binding parameters, such as in drug screening. In another embodiment, the invention can be used to determine the concentration of one or more of the components of the complex. In another embodiment, the method of the invention can be used to determine the thermodynamic parameters of a bimolecular interaction.

In one embodiment, the method of the invention allows for finding $K_d$, $k_{off}$, and/or $k_{on}$ for complex formation from a single electropherogram. In one embodiment, the invention provides a method for finding one, two or all three of said parameters. In one embodiment, the method is a homogenous method. In another embodiment, the components are L and T and the complex is L•T. In yet another embodiment of the method, an equilibrium mixture of said components and complex is subjected to capillary electrophoresis under non-equilibrium conditions. The components and complex are separated by size and charge and detected at a detection point by a detector. The mode of detection can depend on the properties of the components and complex and how or whether the components are labeled. For instance, in one embodiment, one of the components can be fluorescently labeled. In another embodiment, the components and complex can be detected using their native light absorption or fluorescence or electrochemical properties or any combination of them.

The detector can be selected from a variety of types of detectors. In one embodiment, the detector is a UV absorbance detector, which is standard on commercial CE instruments. Many instruments also have diode array detectors available. Alternative detector modes include fluorescence laser-induced fluorescence, and electrochemical detection.

As the components and complex pass through the detector, the time of passage can be recorded to form an electropherogram containing peaks corresponding to the components and complex and exponential curves corresponding to the decay of the complex. However, other methods for recording time of passage of components, complex and rate of decay could also be used. For instance, a detector can be employed that images a large portion or whole length of the capillary. In one embodiment, the peaks and area under the curves in the electropherograms can be used to determine relative amounts of the detected component(s) and/or complex, and can be used to form calibration curves and peaks when known amounts of component(s) and/or complex are present. In another embodiment, these calibration curves and peaks can then be used to determine the concentrations or relative amounts of the components and/or complex in mixtures where these concentrations or relative amounts are not known. In another embodiment the concentration of a component can be determined by first establishing the equilibrium dissociation constant of the bimolecular interaction of the components and using the dissociation constant to determine the unknown concentration of the component. In one embodiment, the complex only slightly decays, considerably decays or completely decays during NECEEM.

In one embodiment of the invention, only one of the components is detected. In another embodiment both components are detected.

In one embodiment, the CE is coupled directly to another device, such as a thermocycler or a mass spectrometer. The hyphenation of CE and mass spectrometers is frequently used to give structural information on the resolved peaks. In another embodiment, the detectors can be interfaced with data acquisition devices to process results.

The peaks and curves of the resulting electropherograms can be used to determine the kinetic parameters of the complex or bimolecular interaction.

In one embodiment the equilibrium mixture is prepared in an electrophoresis run buffer. In another embodiment, the run buffer is free of said components and complex. In another embodiment the run buffer is optimized to separate the complex from said components in capillary electrophoresis. In another embodiment the run buffer contains a mediator that enhances electrophoretic separation of the complex from components.

In one embodiment the method of the invention can be used to determine the temperature of said capillary. This can be done by measuring the equilibrium and/or kinetic parameters of complex formation at different temperatures of said equilibrium mixture and/or said capillary. Thermodynamic parameters, such as enthalpy, the change of entropy and activation energies of the formation and decay of said complex can be determined. Calibration parameters can be determined at known temperatures and can be used to determine unknown temperatures.

In yet another embodiment, the invention provides a method selecting a ligand, L, that binds the target, T, with specified binding parameters, $K_d$, $k_{on}$, and/or $k_{off}$ of the formation of complex between the ligand and target using the aforementioned method for determining said kinetic parameters. In one embodiment, the ligand can be selected from a sample comprising a plurality of ligands with different binding parameters. In another embodiment, more than one ligand can be selected. In yet another embodiment, the method comprises:
 (a) preparing and equilibrating, e.g. incubating, a mixture comprised of said sample and target, wherein the concentration of said target and the time of said equilibration are defined by the desired values of: (i) the equilibrium dissociation constants of said complex and (ii) the bimolecular rate constant of the formation of said complex;
 (b) subjecting said equilibrium mixture to capillary electrophoresis, such as by injecting a plug of said equilibrium mixture into a capillary filled with the buffer solution free of the components of said sample, wherein said capillary is a part of the capillary electrophoresis instrument, wherein said buffer solution is the electrophoresis run buffer; wherein said run buffer is optimized to separate said sample from said target; wherein such run buffer is optimized not to separate the components of said sample and applying voltage to the ends of said capillary and subjecting the components of said equilibrium mixture to capillary electrophoresis;
 (c) collecting fractions eluting from said capillary in different time windows, wherein said time window defines the values of said binding parameters.

In one embodiment, the buffer solution is free of said target. In another embodiment, said buffer solution contains said target. In one embodiment, the fraction is collected in a specific time window in said electrophoresis. In another embodiment, said time window excludes the electrophoretic peak of said sample, yet in another embodiment, the time window includes the electrophoretic peak of said sample.

In yet another embodiment, said time window includes the electrophoretic peak of said complex.

In one embodiment, the sample is a biological sample. In another embodiment, the sample is a combinatorial library, such as a library of oligonucleotides. In another embodiment, aptamers are selected from said library.

In yet another embodiment, the run buffer contains a mediator, which enhances electrophoretic separation of the components of said sample from said complex.

In another embodiment, the method of the invention is applied to the sample that was pretreated prior to the preparation of the equilibrium mixture, such as by the enrichment of the sample with the ligands using another binding assay. In one embodiment, the sample is a library of oligonucleotides and the binding assay is a heterogeneous method of enriching the population of oligonucleotides ligands in the library.

In another embodiment, the method of the invention is applied to a mixture of targets. In another embodiment, the complexes of the ligands and targets have different migration times in capillary electrophoresis. In another embodiment, the complexes are collected in different time windows in capillary electrophoresis. In yet another embodiment, the complexes are identified using another analytical method, for example, but not limited to one of the following: immunoassay, liquid chromatography, affinity chromatography, capillary affinity electrophoresis, and mass spectrometry.

In one embodiment, the migration time of the target is determined in a separate capillary electrophoresis run.

In yet another embodiment the capillary in the aforementioned methods of the invention is a channel of a microfabricated device.

In another embodiment the target is a protein, for example protein farnesyltransferase.

In one embodiment of the methods of the invention, the inner surface of the capillary is coated.

In one embodiment of the methods of the invention a mediator added to the buffer to enhance separation is a nucleic-acid binding protein, such as a single-stranded DNA binding protein.

Further Embodiments

In one embodiment, the method is realized in the following way. The complex-forming components are allowed to react and form an equilibrium mixture. This can be done either outside or inside the capillary. If the equilibrium mixture is prepared outside the capillary, a plug of the equilibrium mixture is introduced into the capillary and subjected to capillary electrophoresis under non-equilibrium conditions to permit complex decay and separation of the components and complex. The migration of one or more components and the complex is monitored. In one embodiment, the migration of the components and complex are detected at a detection point to generate an electropherogram that includes peaks and curves, the areas under which represent the amounts of components and/or complex that have passed through said detection point in a certain time interval. In a preferred embodiment, this single electropherogram may contain enough data to obtain all the kinetic parameters. However, a person skilled in the art would appreciate that any detector monitoring system can be used that enables the determination of amounts (actual or relative) of the components and complex, and rate of decay over time. In a preferred embodiment, the value of $K_d$ can be calculated from the areas under electrophoretic peaks and curves using one of the following two equations:

$$K_d = \frac{A_L A_T}{A_{LT} + A_{decay}}$$

$$K_d = \frac{[T]_0 \left(1 + \frac{A_L}{A_{LT} + A_{decay}}\right) - [L]_0}{1 + 1 \bigg/ \frac{A_L}{A_{LT} + A_{decay}}}$$

wherein $A_T$, $A_L$, and $A_{L \cdot T}$ are areas of peaks corresponding to complex-forming components named T and L, and complex L•T, respectively; $A_{decay}$ is the area under the curve corresponding to the decay of complex L•T. $[T]_0$ and $[L]_0$ are total concentrations of the two components in the equilibrium mixture. The areas are normalized with respect to specific detection properties of T and L, such as extinction coefficients, quantum yields, and electrochemical potentials. The first equation is applicable to cases when both L and T are detectable. The second one is applicable to cases when only one component, L, is detectable. Then in this embodiment, the value of $k_{off}$ can be determined by fitting the decay curve with a single-exponential function:

$$I_t = I_{t_0} \exp\left\{k_{off} \frac{t_{LT}}{t_C - t_{LT}}(t - t_0)\right\}$$

If the fitting is impossible due to contamination of the components that causes additional peaks in the area of the decay curve, then $k_{off}$ can be calculated based on the analysis of the areas:

$$k_{off} = \frac{\ln((A_{LT} + A_{decay})/A_{LT})}{t_{LT}}$$

In the last two formulas, $t_0$ and $t$ are initial and variable time points on the decay curve of L•T; $t_C$ is the migration of one of the component, whose signal constitutes the curve; $t_{L \cdot T}$ is the migration time of L•T capillary electrophoresis. Finally, $k_{on}$ can be determined using the following equation:

$$k_{on} = k_{off}/K_d$$

The method is applicable to components of different nature and origin. For example, a component can be an organic molecule, protein, peptide, enzyme, nucleic acid, aptamer, organelle, cell, virus, particle, or other reagent separable by capillary electrophoresis. If necessary, the component may be pretreated using different procedures such as, but not limited to: lysis, freeze-thaw, centrifugation, enrichment or fractionation. The components can be detected using light absorption, fluorescence, electrochemical properties, radioactivity, mass or charge properties. If the component is not detectable it can be labeled with a tag that facilitates one of the listed above modes of detection. The electrophoresis parameters are optimized to facilitate separation of the components from the complex. This optimization can include modifications to the voltage, temperature, buffer composition (including separation-enhancing mediators), buffer pH, capillary dimensions (including length, inner and outer diameters, material the capillary is made of, capillary pretreatment such as siliconization. If kinetic parameters are measured at different temperatures, then thermodynamic parameters, such as reaction enthalpy, the change of entropy, and activation energies of the formation and decay of the complex can be determined by a person skilled in the art of CE. These thermodynamic parameters can further serve as an indicator of temperature in an electrophoresis device, in which temperature is not controlled.

In another embodiment, the method of the invention allows for the determination of an unknown concentration of target (T) molecules using CE and affinity probe (L) whose complexes with the target molecules decay partially or completely during the CE process. First, the $K_d$ value of complex formation between T and L is determined as described in the previous paragraph, using known concentrations of T and L. Then, an equilibrium mixture comprised of an unknown concentration of T and a known concentration of L is subjected to CE under non-equilibrium conditions optimized by the operator to separate the complex L•T from L. The electropherogram that may contain peaks of L and L•T and a curve corresponding to the decay of L•T are analyzed to determine the unknown concentration of T:

$$[T]_0 = K_d \bigg/ \frac{A_L}{A_{LT} + A_{decay}} + [L]_0 \bigg/ \left(1 + \frac{A_L}{A_{LT} + A_{decay}}\right)$$

where $A_L$ and $A_{L \cdot T}$ are the areas under the peaks corresponding to L and L•T, respectively $A_{decay}$ is the area under the curve corresponding to the decay of L•T during capillary electrophoresis; $[T]_0$ and $[L]_0$ are total concentrations of the two components in the equilibrium mixture. T can be, for example, an organic molecule, protein, peptide, enzyme, nucleic acid, aptamer, organelle, cell, virus, particle, or other reagent separable by capillary electrophoresis. L can be any chemical entity that binds the target with required specificity and affinity. If necessary, T may be pretreated using different procedures such as, but not limited to: lysis, freeze-thaw, centrifugation, enrichment or fractionation. L can be detected using light absorption, fluorescence, electrochemical properties, radioactivity, mass or charge properties. If L is not detectable it can be labeled with a tag that facilitates one of the above listed modes of detection. The electrophoresis parameters are optimized to facilitate separation of L from L•T. This can include modifications to the voltage, temperature, buffer composition (including separation-enhancing mediators), buffer pH, capillary dimensions (length, inner and outer diameters), capillary material, or capillary pretreatment such as siliconization. Alternatively to measuring $K_d$, a calibration curve $A_L/(A_{L \cdot T} + A_{decay})$ vs. [T] can be built. The method can be used as a diagnostic tool to measure the concentration of T present in a patient or biological sample.

In another embodiment, the method of the invention allows for screening and selecting target (T) binding molecules (L), in a fashion that overcomes some of the previously listed problems with using CE. In particular, the method of the invention allows for: (i) selecting L with a specified range of $K_d$, $k_{off}$, and $k_{on}$ values and/or (ii) selecting L when L constitutes only a very small fraction of the total sample and/or (iii) selecting L when T is only available in very small amounts. In one embodiment, the method is realized as follows. First, an equilibration mixture comprised of a sample and T is prepared outside or inside the capillary. The concentration of T and the time of equilibration are defined by the operator depending on the desired values of $K_d$ and $k_{on}$. In the initial selection, ligands with $K_d<K_d^{max}=[T]_1$ and $k_{on}>k_{on}^{min}=1/[T]_1t_{eq1}$ are selected. To achieve this, the equilibrium mixture contains a concentration of T equal to $[T]_1$ and is equilibrated for time equal to $t_{eq1}$. In the following step the ligands with $K_d>K_d^{min}=[T]_2$ and $k_{on}<k_{on}^{max}=1/[T]_2t_{eq2}$ are selected. To achieve this, the equilibrium mixture contains a concentration of T equal to $[T]_2$ and is equilibrated for time equal to $t_{eq2}$. In general, $[T]_2<[T]_1$ and $t_{eq2}<t_{eq1}$. If the equilibrium mixture is prepared outside the capillary, a plug of the mixture is introduced into the capillary and subjected to capillary electrophoresis under non-equilibrium conditions. The electrophoresis conditions are optimized to separate the sample from T but not to separate the components of the sample. Fractions eluting from said capillary are collected at different time windows, which define the values of $K_d$, $k_{on}$, and $k_{off}$ of the collected ligands. T can be an organic molecule, protein, peptide, enzyme, nucleic acid, aptamer, organelle, cell, virus, particle, or other reagent separable by capillary electrophoresis. L can be any chemical entity that binds the target with the required specificity and affinity. L may be a component of a biological sample, patient sample, combinatorial library or other complex mixture. If necessary, T and the sample may be pretreated using different procedures such as, but not limited to: purification, enrichment, fractionation, lysis, freeze-thaw, and centrifugation. Advantageously, T does not need to be detectable. L and the other components of the sample can be detected using light absorption, fluorescence, electrochemical properties, radioactivity, mass or charge properties. If L is not detectable it can be labeled with a tag that facilitates one of the above listed modes of detection. The electrophoresis parameters are optimized to facilitate separation of L from L•T. This optimization can include modifications to the voltage, temperature, buffer composition (including separation-enhancing mediators), buffer pH, capillary dimension (length, inner or outer diameter) capillary material, or capillary pretreatment such as siliconization. When the sample is a combinatorial library of oligonucleotides, the method of the invention can be used to select aptamers that bind T with specific $K_d$, $k_{on}$ and $k_{off}$ values. PCR amplification of collected fractions can be used to amplify collected aptamers. For example, the method of the invention was used to select aptamers to protein farnesyltransferase. When selecting aptamers from oligonucleotide libraries, a single-stranded DNA-binding protein can be used to facilitate the separation of single stranded oligonucleotides from the aptamer-target complexes. When the sample is a combinatorial library containing potential therapeutic agents, the method of the invention can be used to select drug candidates or diagnostic probes that bind the therapeutic target with specific $K_d$, $k_{on}$ and $k_{off}$ values. When the sample is a biological sample, the method of the invention can be used to select natural agents capable of binding T with specific $K_d$, $k_{on}$ and $k_{off}$ values. The method of the invention can be applied to individual or multiple targets. To characterize the selected L, other analytical methods, such as immunoassay, liquid chromatography, affinity chromatography, capillary affinity electrophoresis, PCR, or mass spectrometry can follow the method of the invention. To further improve the efficiency of such combined methods an analytical device can be directly attached to the CE instrument. In a further embodiment, the method of the invention can be performed under equilibrium conditions when the electrophoresis buffer contains T. To conclude, the method of the invention advantageously allows blind selection of ligands when the concentrations of the target and ligands are below the limit of detection. The invention can be utilized even if only single molecules of ligand or target are present, as their detection is not required. This flexibility is essential for selecting ligands with desirable $K_d$, $k_{on}$ and $k_{off}$ values as well as for selecting ligands when T is only available in small amounts or when L represents only a small fraction of the total sample, such as aptamers selected from a combinatorial library (a candidate aptamer may constitute as low as $10^{-13}$ of the sample (Gold, J. Biol. Chem. 270, 1995, 13581).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

FIG. 4 is a schematic representation of a NECEEM electropherogram during the selection of ligands with $K_d<K_d^{max}=[T]_1$ and $k_{on}>k_{on}^{min}=1/[T]_1t_{eq1}$, when the migration time of the target is known. Ligands are collected between $t_T$ and $t_L$ from one side of peak L, which corresponds to the sample. They are collected to the left of peak L, if $t_T<t_L$ (Panel A) and to the right of peak L, if $t_T<t_L$ (Panel B).

FIG. 6 is a schematic representation of a NECEEM electropherogram during the selection of ligands with $k_{off}<k_{off}^{max}=1/t_{L•T}$ (Panel A), and $1/t_2=k_{off}^{min}<k_{off}<k_{off}^{max}=1/t_1$ (Panel B).

DETAILED DESCRIPTION OF THE INVENTION

Definitions

Figure 1:
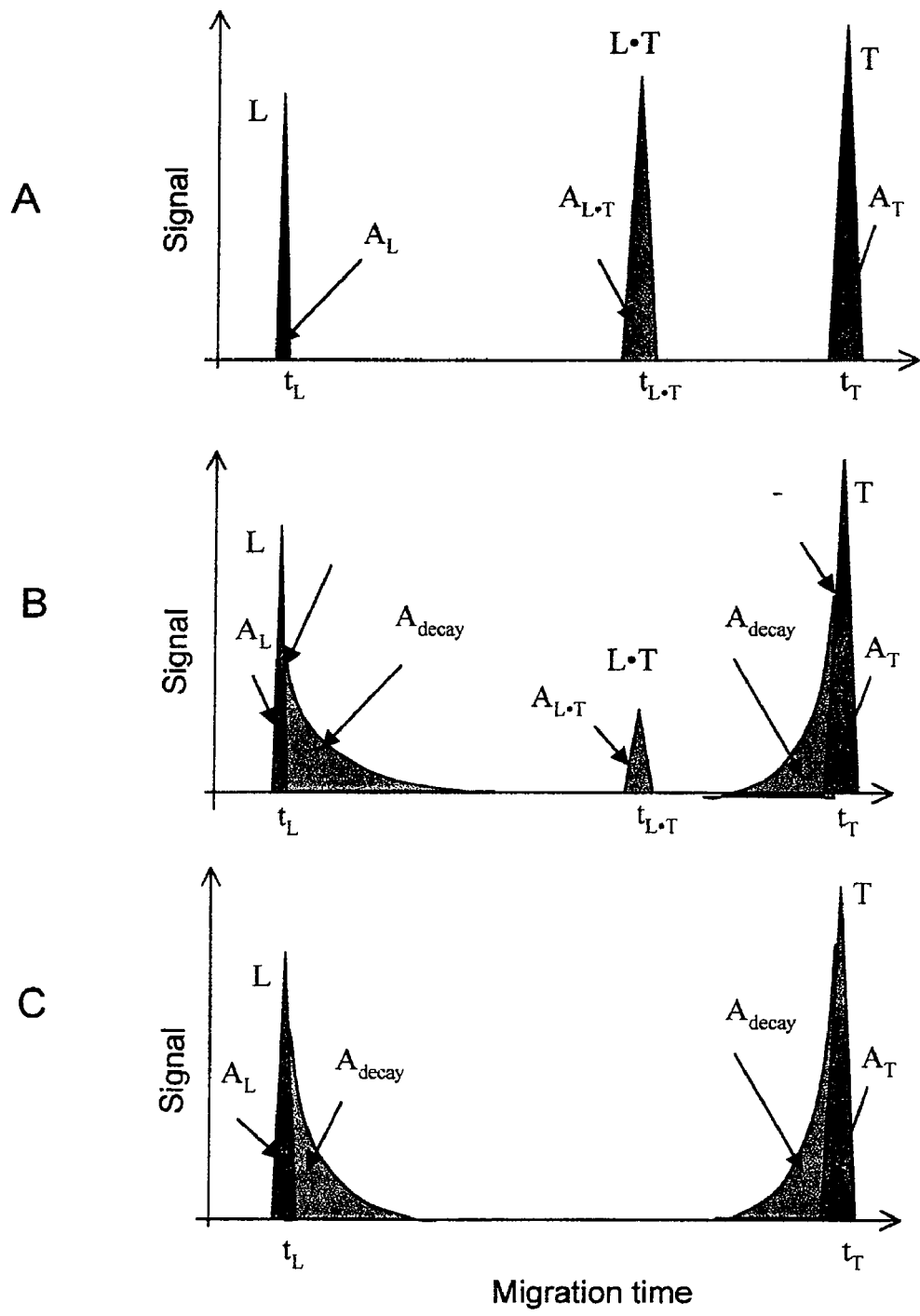
FIG. 1 is a schematic representation of NECEEM electropherograms when both L and T are detectable. Panels A, B and C correspond to low, intermediate, and high $k_{off}$ values, respectively. Due to undetectable complex decay in panel A, NECEEM converges into an ordinary equilibrium CE.

ACE—affinity capillary electrophoresis, the mode of capillary electrophoresis in which one of the complex-forming components is added to the separation buffer to maintain the equilibrium during the course of CE separation.

Aptamer as used herein means a binding partner that is selected from a combinatorial library that is nucleotide- or peptide-based. Aptamers are characterized by high selectivity and high affinity towards the targets they are selected for. Due to these properties aptamers are often viewed as artificial antibodies.

Bimolecular interaction is a reaction between 2 chemical entities or components. Each entity can itself comprise more than one component. The pairs of interacting entities include but are not limited to: protein and protein, protein and nucleic acid, protein and aptamer, enzyme and substrate, antigen and antibody, drug and therapeutic target, affinity probe and diagnosed molecule, hybridization probe and target nucleic acid sequence, etc.

CE—capillary electrophoresis

Combinatorial library as used herein means a collection of synthetic components that are produced by randomized synthesis. For example, combinatorial libraries of oligonucleotides or peptides consist of oligonucleotides or peptides of randomized sequence compositions. Combinatorial libraries can also be comprised of small organic molecules of randomized structure. The library can comprise multiple different ligands or targets. They can be from a biological sample. In one embodiment, the library is a library of chemical compounds, organic molecules, peptides, or nucleic acids.

Component as used herein refers to a chemical entity or substance that can interact with at least one other chemical entity or substance to form a complex comprising two components. Each entity itself can comprise one or more dNTP—deoxynucleotide triphosphate dsDNA—double stranded deoxyribonucleic acid Dynamic range as used herein means the range of concentrations of target within which the method works.

Electropherogram as used herein means the time-dependent signal produced in a capillary electrophoresis. The signal is sensed by a detector placed at a certain point along the length of the capillary or past the capillary. The intensity of the signal, when properly normalized, is proportional to the concentration of detected species. The integrated signal (or the area under the line in the electropherogram) for the time window $t_1$-$t_2$ represents the amount of the species that passed the detector in this time window.

$t_{eq}$—Equilibration time as used herein means incubation time of the equilibrium mixture from the point of mixing components to the beginning of NECEEM. Equilibration time defines the ligands that are capable of binding the target. The ligands with $k_{on}>1/[T]t_{eq}$ will preferably equilibrate with the target within equilibration time $t_{eq}$, while those with $k_{on}<1/[T]t_{eq}$ will not reach equilibrium.

Equilibrium as used herein relates to the reaction of complex formation and means a state wherein the rate of complex formation is equal to complex decay so that the concentration of the components and complex do not change with time. Conditions that facilitate the maintenance of equilibrium are said to be equilibrium conditions. An equilibrium mixture or equilibrium composition as used herein refers to a composition comprising both components and the complex in a state of equilibrium (i.e. where the concentrations remain relatively stable or unchanged over time).

fDNA—is a fluorescently labeled DNA, such as 5'-fluorescein-GCGGAGCGTGGCAGG (SEQ ID NO:1).

Heterogeneous Assay as used herein is an assay wherein on of the interacting components is affixed to a solid substrate. In this case the interaction between the components is realized on the surface. Since the concentration of the affixed component on the surface is not defined, many aspects of standard kinetics are not applicable to heterogeneous assays. component on the surface is not defined, many aspects of standard kinetics are not applicable to heterogeneous assays.

Homogeneous Assay as used herein is an assay wherein the components form complexes in solution and neither of the interacting components (target and ligand) is affixed to a solid substrate. Standard homogeneous kinetics based on the concentration of the components is applicable to homogeneous assays.

I.D.—inner diameter $K_d$ as used herein means the equilibrium dissociation constant of a complex measured in mol/L or M.

$k_{off}$ as used herein means the monomolecular rate constant of complex decay measured in $s^{-1}$.

$k_{on}$ as used herein means the bimolecular rate constant of complex formation measured in $mol^{-1} Ls^{-1}$ or $M^{-1} s^{-1}$.

kPa—kilopascals kV—kilovolts

L—ligand as used herein, in very general terms means one of two interacting components (the second component is called target herein). In one embodiment a ligand can be either the affinity probe, or a target-binding molecule, which is selected from a sample. For example, an aptamer selected from a combinatorial library of oligonucleotides is a ligand, while the molecule which the aptamer binds specifically, is its target. Another example of a ligand is a drug candidate that binds its therapeutic target. In another embodiment, it can be, but is not necessarily limited to a molecule, protein, nucleic acid, aptamer, organelle, virus, bacterium, cell, particle or combination thereof.

[L]—concentration of L

L•T—dynamic complex of L and T

Large Combinatorial Library as used herein is a combinatorial library in which the probability of any molecule to be unique is greater than 99%.

Microfabricated device as used herein is a device that contains a micro-channel, which can serve as a capillary for CE.

Migration time as used herein means the time required by a chemical entity subjected to CE, to reach the detector. Migration time is influenced by a number of parameters, such as electric field, composition and pH of CE run buffer, modification of capillary walls, etc.

NECEEM—Non-equilibrium capillary electrophoresis of equilibrium mixtures is capillary electrophoresis, in which an equilibrium composition of components and complexes are subjected to electrophoresis under conditions that promote decay of the complexes loaded therein.

Non-equilibrium as used herein refers to a state wherein the components and complex of a reaction are not in equilibrium, such that concentrations of each of the components and complex are not stable, e.g. in a state of fluctuation. Conditions that cause the equilibrium not to be maintained are said to be non-equilibrium. For example, conditions that promote decay of a complex are non-equilibrium conditions; under such conditions the concentration of the complex is decreasing while the concentration of free components is increasing during the decay process over time. Non-equilibrium conditions can be induced by the removal of one or more components from the equilibrium mixture.

O.D.—outer diameter

PCR—polymerase chain reaction

PFTase—protein farnesyltransferase

Plug as used herein means the solution injected into the capillary psi—pounds per square inch Sample as used herein means a composition that can be natural, biological or synthetic that may contain potential ligands.

SSB—single-stranded DNA binding protein from *E. coli* ssDNA—single stranded deoxyribonucleic acid

T—target as used herein, means one of two interacting components (the second component is called ligand herein). In one embodiment it can be either the component whose concentration is to be determined, or the component for which another component (ligand) is to be selected from a sample. For example, a therapeutic target is a molecule, such as protein, with which a drug candidate can target can be, but is not necessarily limited to a molecule, protein, nucleic acid, aptamer, organelle, virus, bacterium, cell, particle or combination thereof.

[T]—concentration of T $t_C$—migration time of one of components (C)

$t_L$—migration time of L $t_T$—migration time of T $t_{L \cdot T}$—migration time of L•T

DESCRIPTION

Capillary electrophoresis (CE) has proved to be a very efficient analytical tool exhibiting high resolution, high sensitivity, high speed, and requiring only minimal amounts of sample. The method of this invention is based on a new CE approach, termed Non-Equilibrium Capillary Electrophoresis of Equilibrium Mixtures (NECEEM). NECEEM is based on the inventors' finding that the advantages of equilibrium and non-equilibrium conditions can be combined in a single capillary electrophoresis procedure to provide the foundation of three practical applications. Conceptually in NECEEM, an equilibrium mixture of molecules T (Target) and L (Ligand), is prepared by mixing them and allowing them, outside or inside the capillary, to reach equilibrium as described by equation 1:

$$L + T \underset{k_{off}}{\overset{k_{on}}{\rightleftharpoons}} L \cdot T \quad (1)$$

The concentrations of L, T, and L•T in the equilibrium mixture are defined by $K_d$. If the equilibrium mixture is prepared outside the capillary, a plug of the mixture is introduced into the capillary preferentially by pressure (electrokinetic introduction can disturb equilibrium) and subjected to electrophoresis under non-equilibrium conditions, using a separation buffer. In one embodiment, the separation buffer contains neither L nor T. The separation conditions are optimized so that at least two of the three components L, T and L•T, are effectively separated. Under such conditions at least one of L and T is continuously removed from the electrophoretic zone of L•T and such removal causes continuous monomolecular decay of L•T with the rate constant $k_{off}$. Electrophoretic data generated by NECEEM are comprised, in general, of three peaks and two curves (FIG. 1). Two peaks correspond to equilibrium fractions of L and T and one peak to non-decayed L•T. The curves correspond to L and T produced by the decay of L•T. The number of peaks and curves may be fewer if only one of the two components, L or T, is detectable (e.g. has a fluorescent label or other detectable property or label (see examples 2 and 8)), or if L•T decays to undetectable levels upon reaching the detector (see examples 1C, 2C, 9, and 13). Due to the mixed equilibrium/non-equilibrium nature of NECEEM, the electrophoretic data contains accurate information about both $K_d$ and $k_{off}$. This feature of NECEEM forms the basis of the applications disclosed in this application.

This document discloses three practical applications of the NECEEM-based method. In the first application, the method of the invention facilitates finding kinetic and thermodynamic parameters of complex formation. It advantageously allows for revealing two parameters, the equilibrium dissociation constant, $K_d$, and the monomolecular rate constant of complex decay, $k_{off}$, from a single electropherogram. In the second application, the method of the invention provides an approach for quantitative affinity analysis of target molecules. It facilitates the use of affinity probes with relatively high values of $k_{off}$ ($k_{off} > 10^{-2}$ s$^{-1}$) in such analyses. In the third practical application, the method of this invention presents a new and powerful approach to select target-binding molecules (ligands) from complex mixtures. Unique capabilities of the method of the invention with respect to the third application include but are not limited to: (a) the selection of ligands with specified ranges of kinetic and thermodynamic parameters of target-ligand interactions, (b) the selection of ligands present in minute amounts (even as low as 1 molecule) from complex mixtures of biological or synthetic samples, and (c) the selection of ligands for targets available in very low amounts (again as few as 1 molecule). The advantages of the method of the invention are based on the homogeneous nature and their ability to combine equilibrium and non-equilibrium conditions in a single CE run. The three applications of this invention can be used for discovery and characterization of drug candidates and the development of new diagnostic tools.

Application 1. Determination of $K_d$ and $K_{off}$ of Complex Formation from a Single NECEEM Electropherogram In one embodiment of this invention, the equilibrium mixture of molecules T and L (for which $K_d$ and $k_{off}$ are to be determined) is prepared by mixing T and L outside or inside the capillary and allowing them to reach equilibrium (see equation 1 above). The equilibrium mixture can be prepared inside the capillary by, for example, introducing a plug of the component with lower electrophoretic mobility first, and the component with greater electrophoretic mobility second. The components are mixed by applying voltage to the capillary. If the equilibrium mixture is prepared outside the capillary, a plug of the equilibrium mixture is injected into the capillary, preferably by pressure (injection by voltage can disturb the equilibrium). The equilibrium mixture contains three components: free L, free T, and the L•T complex. The equilibrium mixture is subjected to electrophoresis using a run buffer that does not contain L or T or L•T. The conditions for electrophoresis are optimized (by finding the appropriate run buffer or modifying the surface of inner capillary walls or other means) so that L and T have different mobilities. The complex will typically have an intermediate mobility. Thus, the equilibrium fraction of at least one of L or T is removed from the electrophoretic zone of the L•T complex as soon as electrophoresis starts. The equilibrium fractions of L and T migrate as single electrophoretic zones and result in two peaks. The equilibrium fraction of the L•T complex cannot generate a single electrophoretic peak since the equilibrium of the complex is not maintained in NECEEM. The complex continuously decays during the separation resulting in the non-equilibrium production of free L and free T. According to equation 1, the rate of L and T production reduces exponentially following the monomolecular decay of the complex during NECEEM separation:

$$\frac{d[L]}{dt} = \frac{d[T]}{dt} = -\frac{d[L \cdot T]}{dt} = [L \cdot T]_{eq} \exp(-k_{off} t) \qquad (3)$$

Here $[L \cdot T]_{eq}$ is the equilibrium concentration of the complex in the equilibrium mixture and t is the time from the beginning of separation. In general, the monomolecular decay, represented by equation 3, produces two exponential curves in the electropherogram (FIG. 1). Finally, complex, that remains intact at the time it passes the detector, generates another peak.

To represent true concentrations of the species, signal intensities and areas in electropherograms must be properly normalized. The approaches of normalization are well known to a person of ordinary skills in the art of CE. Briefly, if absorption detection is used then the areas are normalized by the extinction coefficients of L and T at the wavelength or wavelengths of detection. If fluorescence detection is used, then the areas are normalized by quantum yields of L and T. If on-column detection is used then, the areas must be normalized by the migration velocities as well. In the case of past-column sheath flow detection, no normalization of migration velocities is required since all components pass the detector with the same velocity defined by the sheath-flow velocity. In this application it is assumed that the intensities and the areas in the electropherograms are properly normalized.

Depending on whether one or both of L and T are detectable, two situations may occur.

The first situation is presented in FIG. 1. This figure schematically illustrates the important features of a NECEEM electropherogram when both L and T are detectable (e.g. diode array detector is used). Depending on the values of $k_{off}$ and the migration time, $t_{L \cdot T}$, of the L•T complex, the complex decays to different degrees during its migration through the capillary.

If $k_{off} \ll 1/t_{L \cdot T}$ then no detectable decay will be observed and, in general, the electropherograms will be comprised of three peaks corresponding to L, T, and L•T (FIG. 1A). Since no complex decay is observed, NECEEM converges into an ordinary equilibrium CE of complexes, which is described in detail in prior art articles. The areas correspond to equilibrium concentrations of L, T, and L•T: $[L]_N$, $[T]_{eq}$, and $[L \cdot T]_{eq}$. The value of $K_d$ can be found as:

$$K_d = \frac{[L]_{eq}[T]_{eq}}{[L \cdot T]_{eq}} = \frac{A_L A_T}{A_{LT}} \qquad (4)$$

where $A_T$, $A_L$, and $A_{L \cdot T}$ are the areas of the peaks corresponding to T, L, and L•T, respectively. To measure $k_{off}$, the conditions (buffer, capillary length, capillary coating, pressure, etc.) of CE must be changed to increase $t_{L \cdot T}$ in order to operate under the conditions of NECEEM.

If $k_{off}$ and $1/t_{L \cdot T}$ are of the same order of magnitude, then complex decay is considerable but the peak corresponding to intact L•T is still detectable. These are the conditions of NECEEM. The NECEEM electropherogram in such a case consists of 3 peaks and two decay areas (FIG. 1B). The value of $K_d$ can be found from a single NECEEM electropherogram as:

$$K_d = \frac{[L]_{eq}[T]_{eq}}{[L \cdot T]_{eq}} = \frac{A_L A_T}{A_{LT} + A_{decay}} \quad (5)$$

where the equilibrium concentration of the complex $[L \cdot T]_{eq}$ is represented by the sum of the two areas, $A_{L \cdot T}$ and $A_{decay}$. The two decay areas in FIG. 1B are identical since they represent a single process of decay. Only one area is included in equation 5. The value of $k_{off}$ is found by analyzing the decay data. Three approaches are suggested here.

In the first approach, a decay line, which defines one of the decay areas, is fitted with a single-exponential function and $k_{off}$ is obtained from this fitting:

$$I_{tL} = I_{t_0^L} \exp\left\{ k_{off} \frac{t_{LT}}{t_L - t_{LT}} (t^L - t_0^L) \right\} \quad (6)$$

for the decay followed by the production of L or $$I_{tT} = I_{t_0^T} \exp\left\{ k_{off} \frac{t_{LT}}{t_T - t_{LT}} (t^T - t_0^T) \right\} \quad (7)$$

for the decay followed by production of T. In the two last equations the following notations are used: $I_{t^L}$ and $I_{t^T}$ are the signal intensities at time t corresponding to L and T, respectively; $I_{t_0^L}$ and $I_{t_0^T}$ are initial signal intensities at times $t^L_0$ and $t^T_0$, respectively; $t_L$, $t_T$, and $t_{L \cdot T}$ are migrations times of L, T, and L•T, respectively.

In the second approach, $k_{off}$ can be found from the same lines by using one of the following 2 equations:

$$k_{off} = \frac{\ln(I_{tL}/I_{t_0^L})}{t_{LT}(t_L^L - t_0^L)/(t_L - t_{LT})} \quad (8)$$

or $$k_{off} = \frac{\ln(I_{tT}/I_{t_0^T})}{t_{LT}(t^T - t_0^T)/(t_T - t_{LT})} \quad (9)$$

where $t^L$ and $t^T$ are fixed time points on the two lines. Formulas 8 and 9 were obtained by taking the natural log(ln) function of equations 6 and 7.

In the third approach, if the L•T peak is detectable, then $k_{off}$ can be found by analyzing only the areas:

$$k_{off} = \frac{\ln((A_{LT} + A_{decay})/A_{LT})}{t_{LT}} \quad (10)$$

The last approach is especially useful when the exponential line is "contaminated" so that fitting is problematic. The three described approaches can be modified in a number of ways by a person skilled in the art of CE.

If $k_{off} \gg 1/t_{L \cdot T}$, then the complex decays to undetectable levels during its migration through the capillary. No peak corresponding to L•T is observed. The electropherogram in such a case consists of 2 peaks and two decay areas (FIG. 1C).

The value of $K_d$ can be found as:

$$K_d = \frac{[L]_{eq}[T]_{eq}}{[L \cdot T]_{eq}} = \frac{A_L A_T}{A_{decay}} \quad (11)$$

where the equilibrium concentration of the complex $[L \cdot T]_{eq}$ is represented by a single area of complex decay, $A_{decay}$. The value of $k_{off}$ is found by analyzing the decay data and using one of equations 6-9. Since the L•T peak is not detectable under these conditions, information on the value of $t_{L \cdot T}$ cannot be obtained using NECEEM. The NECEEM conditions (separation buffer, capillary coating, pressure) should be changed to shorten the separation time. Alternatively, ACE can be used by a person of ordinary skills in CE to obtain the value of $t_{L \cdot T}$ (Berezovski and Krylov, *Anal. Chem.* 2003, 72, 1982).

Figure 2:
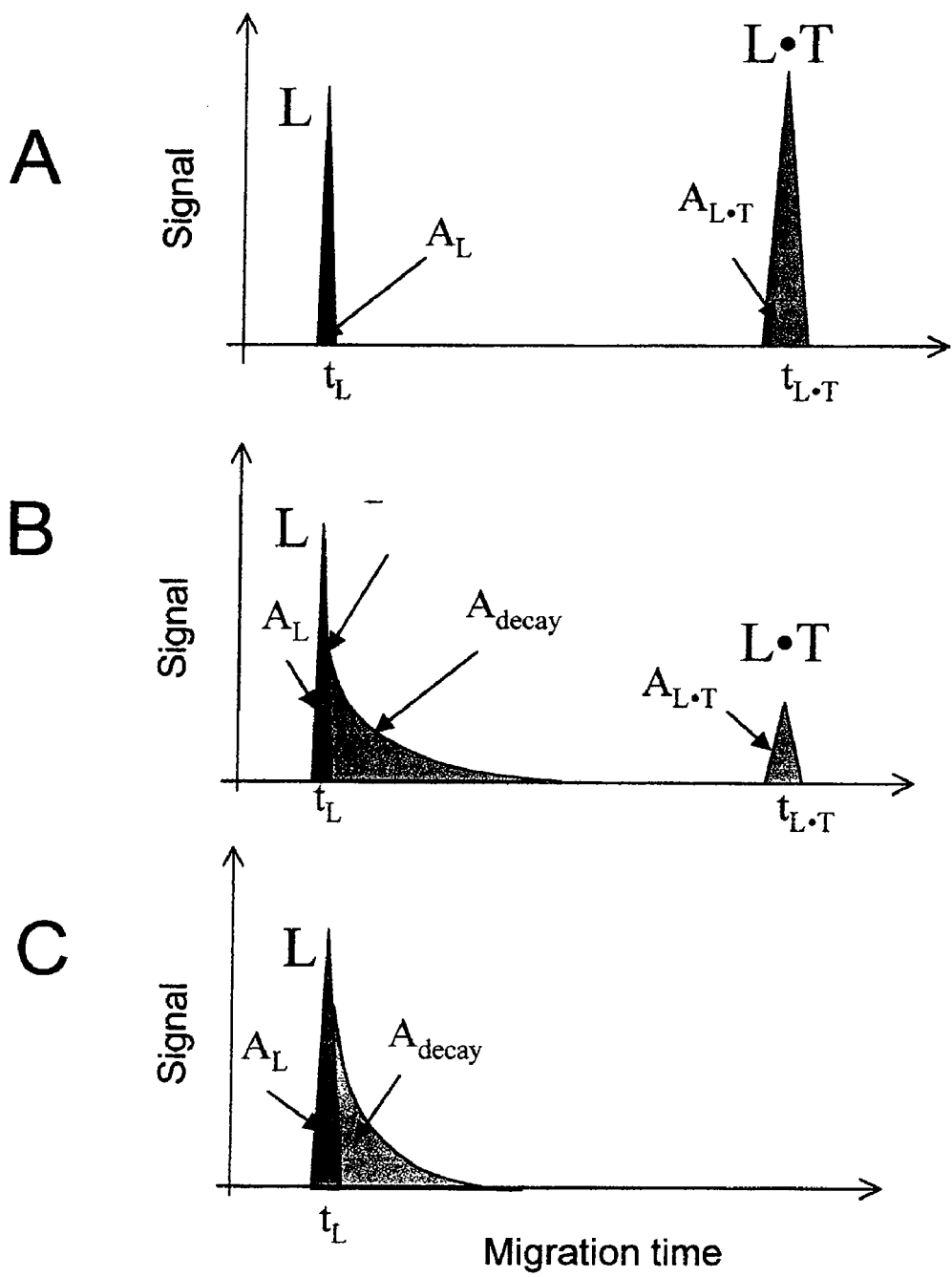
FIG. 2 is a schematic representation of NECEEM electropherograms when only L is detectable. Panels A, B and C correspond to low, intermediate, and high $k_{off}$ values, respectively. Due to undetectable complex decay in panel A, NECEEM converges into an ordinary equilibrium CE.

The second situation is illustrated by FIG. 2. This figure schematically shows the important features of a NECEEM electropherogram where only L is detectable (e.g. a fluorescence detector is used and only L has a fluorescence label). A similar approach is applicable to the case when only T is detectable. If only L is detectable, then the peak of T will not be present in the electropherograms. Depending on the values of $k_{off}$ and the migration time, $t_{L \cdot T}$, of the L•T complex, the complex decays to different degrees during its migration through the capillary.

If $k_{off} \ll 1/t_{L \cdot T}$, then no detectable decay of L•T is observed. Since no complex decay is observed, NECEEM converges into an ordinary equilibrium CE of complexes, which is described in detail in prior art articles. The CE electropherogram in this case is comprised of two peaks corresponding to L, and L•T (FIG. 2). The areas under the peaks correspond to equilibrium concentrations of L and L•T: $[L]_{eq}$ and $[L \cdot T]_{eq}$, respectively. Thus, a ratio of the two concentrations can be experimentally found:

$$R = \frac{[L]_{eq}}{[L \cdot T]_{eq}} = \frac{A_L}{A_{LT}} \quad (12)$$

and the value of $K_d$ can be calculated according to the following equation (for the derivation see supplementary material to Berezovski and Krylov, *Analyst* 2003, 128, 571):

$$K_d = \frac{[T]_0(1 + R) - [L]_0}{1 + 1/R} \quad (13)$$

where $[T]_0$ and $[L]_0$ are total concentrations of T and L in the equilibrium mixture. To measure $k_{off}$, the NECEEM conditions (separation buffer, capillary length, capillary coating, pressure, etc.) must be changed to increase $t_{L \cdot T}$.

If $k_{off}$ and $1/t_{L \cdot T}$ are of the same order of magnitude, then complex decay is considerable but the peak corresponding to the intact L•T is still detectable. These are the conditions of NECEEM. The NECEEM electropherogram in such a case consists of 2 peaks and one decay area (FIG. 2B). The value of $K_d$ can be found using equation 13 and the following formula for the equilibrium ratio between the concentrations of L and L•T:

$$R = \frac{[L]_{eq}}{[L \cdot T]_{eq}} = \frac{A_L}{A_{LT} + A_{decay}} \quad (14)$$

where the equilibrium concentration of complex $[L \cdot T]_{eq}$ is represented by the sum of two areas, $A_{L \cdot T}$ and $A_{decay}$. The value of $k_{off}$ can be found by analyzing the decay data. The approaches described above and formulas 6-10 can be used to find $k_{off}$.

If $k_{off} \gg 1/t_{L \cdot T}$, then the complex decays to undetectable levels during its migration through the capillary. No peak corresponding to L•T is observed. The electropherogram in such a case consists of 1 peak and 1 decay area (FIG. 2C). The value of $K_d$ can be found using equation 13 and the following formula for R:

$$R = \frac{[L]_{eq}}{[L \cdot T]_{eq}} = \frac{A_L}{A_{decay}} \quad (15)$$

where the equilibrium concentration of the complex $[L \cdot T]_{eq}$ is represented by a single decay area, $A_{decay}$. The value of $k_{off}$ is found by analyzing the decay data and by using one of equations 6-9. Since the L•T peak is not detectable in this case, the information on the value of $t_{L \cdot T}$ cannot be obtained from NECEEM under these conditions. The NECEEM conditions (separation buffer, capillary coating, pressure etc.) should be changed to shorten the separation time. Alternatively, ACE can be used by a person of ordinary skills in CE to obtain the value of $t_{L \cdot T}$.

The value of $K_d$ is associated with equilibrium mixture conditions, thus it is determined by the incubation buffer, in which the equilibrium mixture is prepared. The value of $k_{off}$ is associated with separation conditions, thus it is determined by the electrophoresis run buffer, in which complex decay is monitored. If the incubation and run buffers are the same then, the value of $k_{on}$ can be calculated using the following equation:

$$k_{on} = k_{off}/K_d \quad (2a)$$

The method of this invention can be used to determine thermodynamic parameters of reaction 1 if a series of NECEEM procedures are performed at different temperatures. The rate constants and the equilibrium constant are temperature dependent:

$$k_{on} = A_{on} \exp(-E_{a(on)}/RT) \quad (16)$$

$$k_{off} = A_{off} \exp(-E_{a(off)}/RT) \quad (17)$$

$$K_d = \exp\left(\frac{\Delta H^\circ}{R}\frac{1}{T} - \frac{\Delta S^\circ}{R}\right) \quad (18)$$

where $A_{on}$ and $A_{off}$ are pre-exponential factors for the forward and reverse reactions of equilibrium 1, respectively; $E_{a(on)}$ and $E_{a(off)}$ are activation energies for the forward and reverse reactions in equilibrium 1, respectively; $\Delta H^\circ$ is the reaction enthalpy for process 1; $\Delta S^\circ$ is the change of entropy in process 1; R is the gas constant and T is the temperature in Kelvin (Note "R" in equations 12-15 is the ratio of equilibrium concentrations, while "R" in equations 16-18 is the gas constant).

If the equilibrium mixture at different temperatures is analyzed by NECEEM, then $K_d$ can be found as a function of temperature, and $\Delta H^\circ$ and $\Delta S^\circ$ can be determined using equation 18. Similarly, $E_{a(on)}$ and $E_{a(off)}$ can be found using equations 2, 16, and 18 if both $K_d$ and $k_{off}$ are measured as functions of temperature.

One embodiment of the method of the invention provides an indirect way of determining temperature in a capillary or in a channel of a chip-based microseparation system by measuring either $K_d$ or $k_{off}$. A calibration curve $K_d$ vs. T (or $k_{off}$ vs. T) is built using a CE instrument with a reliable temperature control or SPR. Then, $K_d$ (or $k_{off}$) is measured using a CE apparatus or a chip-based system for which the temperature is to be determined. The temperature is determined from the calibration curve by finding the temperature which corresponds to $K_d$ (or $k_{off}$) measured with the instrument in question. Alternatively, the following formula can be used instead of the calibration curve:

$$T = \frac{\Delta H^\circ}{R(\Delta S^\circ R - \ln K_d)} \quad (18a)$$

The method of the invention further provides a unique way for the direct measurement of fluorescence anisotropy of the L•T complex when L is fluorescently tagged. Traditionally, fluorescence anisotropy of an L•T complex is determined from data obtained in a series of anisotropy measurements where the concentration of T in the equilibrium mixture is increased. The equilibrium mixture also contains free L and L•T. To ensure that the majority of L is bound to T, the concentration of T has to be much higher than the $K_d$ of the complex. This constitutes the major disadvantage of traditional methods. High concentrations of T may interfere with fluorescence measurements. Moreover, if T is a protein, high concentrations of T may be difficult to achieve due to solubility problems or due to the cost of using expensive proteins. In one method of the invention, the L•T complex is separated from both the equilibrium fraction of free L and from free L formed during the decay of the complex. Thus, the Loa peak is not "contaminated" with free L and fluorescence anisotropy of the peak corresponds to true fluorescence anisotropy of L•T.

The method of this invention is applicable to finding binding parameters of components of different nature and origin. For example, a component can be an organic molecule, protein, peptide, enzyme, nucleic acid, carbohydrate, aptamer, organelle, cell, virus, particle, or other reagent separable by capillary electrophoresis. If necessary, the component may be pretreated using different procedures such as, but not limited to: purification, enrichment, fractionation, lysis, freeze-thaw, or centrifugation. The components can be detected using their light absorption, fluorescence, electrochemical properties, radioactivity, and mass or charge properties. If the component is not detectable it can be labeled with a tag that facilitates one of the listed above modes of detection. The electrophoresis parameters are optimized to facilitate separation of the components from the complex. This optimization can include modifications to the voltage, temperature, buffer composition (including separation-enhancing mediators), buffer pH, capillary length or width, or capillary pretreatments such as siliconization or covering with dynamic coatings.

The method of this invention in its first application has extremely high sensitivity. If L is fluorescent, and laser-induced fluorescence is used, then as few as $10^{-18}$ moles of T are sufficient to determine the $K_d$ and $k_{off}$ values of its interaction with L. The values of $K_d$ and $k_{off}$ are determined from the analysis of areas in the electropherogram. The value of $k_{off}$ can also be determined by fitting the exponential part of the electropherogram with a single-exponential function. Further the method allows for only one component, L or T, to be detectable. In such a case the method requires that the detectable component be electrophoretically separated from the complex. The method can also be applied to complexes which decay to undetectable levels by the time they reach the detector. If a series of experiments is performed at different temperatures then a number of thermodynamic parameters (activation energies of forward and reverse reactions (see reaction 1), the reaction enthalpy, and the change of entropy) can be determined.

Application 2. Quantitative Analysis of T Using an Affinity Probe L

Another embodiment of the invention is a NECEEM-based method for quantitative affinity analyses of a target molecule, T, using an affinity probe, L. Affinity probes, in general, are molecules that can bind a target with high specificity and with high affinity. Affinity probes are typically tagged with a label (radioactive, fluorescent, enzymatic, etc.) that permits detection of both L and L•T. One widely used example of an affinity probe is antibodies. Another example, which is still relatively new, is oligonucleotide or peptide aptamers (Clark and Remcho, *Electrophoresis* 2002, 23, 1335; WO 0340168; Levy and Ellington, *Biotechnol. Bioengineer.* 2003, 82, 38).

NECEEM of such target-probe pairs generates, in general, electropherograms with two peaks and one exponential curve (see FIGS. 2B and 2C). One peak corresponds to the equilibrium part of the probe, while the second peak corresponds to the non-decayed complex that reaches the detector. The second peak may not be observed if the complex decays to undetectable levels during separation. The exponential part represents free probe produced during the decay of the complex. This application of the method of the invention can be realized by two approaches.

CE has been used for quantitative affinity analyses using labeled affinity probes. If $k_{off}$ is low compared to the reciprocal migration time ($t_m$) of the complex, $k_{off} \ll 1/t_m$, then the complex undergoes no considerable decay during the separation and NECEEM converges into an ordinary equilibrium CE. The unknown concentration of T in the sample can be calculated by determining the areas of the peaks corresponding to L and L•T. If $k_{off} \geq 1/t_{L•T}$, the complex undergoes decay during the separation, which results in a decreased area for the peak corresponding to L•T. If $k_{off} \gg 1/t_{L•T}$, the L•T peak may be absent due to decay of the complex to undetectable levels. Thus, if $k_{off} \geq 1/t_{L•T}$, then traditional equilibrium CE analyses, which rely on measurements of peaks L and L•T only, either lead to underestimated values for unknown T or become completely impossible. This invention provides a NECEEM-based approach that overcomes these problems and facilitates the use of affinity probes with $k_{off} \geq 1/t_{L•T}$ for quantitative affinity analyses by CE.

An equilibrium mixture is prepared for molecules T and L, where T is the target whose concentration is to be measured and L is the detectable affinity probe that binds the target according to equation 1. The equilibrium mixture can be prepared inside or outside the capillary. It can be made inside the capillary by, for example, introducing a plug of the component with lower electrophoretic mobility first, and the component with greater electrophoretic mobility second. The components are mixed by applying voltage to the capillary. If the equilibrium mixture is prepared outside the capillary, a plug of the equilibrium mixture is injected into the capillary, preferably by pressure (injection by voltage can disturb the equilibrium). The equilibrium mixture contains three components: free L, free T and the L•T complex with only L and L•T being detectable. The equilibrium mixture is subjected to electrophoresis under non-equilibrium conditions. The conditions for electrophoresis are optimized so that L and L•T have different mobilities. This optimization can include modifications to the voltage, temperature, buffer composition (including separation-enhancing mediators), buffer pH, capillary length or width, or capillary pretreatment such as siliconization or covering with dynamic coatings. When L leaves the electrophoretic zone of L•T, equilibrium 1 is no longer maintained. If $k_{off} \geq 1/t_{L•T}$, the complex undergoes decay during the separation. Depending on the extent of the decay, one of two types of NECEEM electropherograms, depicted in FIGS. 2B and 2C, is observed.

Two approaches can be used to determine the unknown concentrations of T. The first approach requires that the $K_d$ of complex formation be determined for the interaction of T and L first, using NECEEM as described above. The unknown concentration of T in the sample can then be determined by finding the areas of the three (or two) features in the single electropherogram, and by using a simple mathematical formula that includes the areas, the concentration of the probe, and the value of $K_d$:

$$[T]_0 = K_d/R + [L]_0/(1+R) \qquad (19)$$

where $[L]_0$ is the total concentration of the probe in the sample, R is determined from equations 14 or 15 depending on whether or not the electropherogram obtained exhibits a peak corresponding to L•T. This approach has no restriction on $[L]_0$ and, thus, is universal.

The second approach requires that a calibration curve be built for the signal (the ratio, R, of the areas) as a function of the target concentration. For finding the unknown concentration of T, the areas of the three (or two) features in a single electropherogram are determined, the ratio is calculated and the calibration curve, $A_L(A_{L•T}+A_{decay})$ vs. [T], is used to find the unknown concentration of the target that corresponds to the same ratio, R, of the areas. The "calibration curve" approach requires that the same concentration of L be used for building the calibration curve and for experiments to determine the unknown concentrations of T. The "$K_d$" approach is more universal since different concentrations of L can be used for finding $K_d$ and for finding the unknown concentration of the target.

The method of the invention allows T to be a wide variety of entities including, but not limited to: an organic molecule, protein, peptide, enzyme, nucleic acid, aptamer, organelle, cell, virus, particle, or other reagent separable by capillary electrophoresis. L can be any chemical entity than binds the target with required specificity and affinity. If necessary, T may be pretreated using different procedures such as, but not limited to: purification, enrichment, fractionation, lysis, freeze-thaw, and centrifugation. L can be detected using light absorption, fluorescence, electrochemical properties, radioactivity, mass or charge properties. If L is not detectable, it can be labeled with a tag that facilitates one of the above listed modes of detection.

This method can be used as a diagnostic tool to measure the concentration of T present in a patient or biological sample. The method of the invention in its second application will be applicable to a wide variety of target-probe pairs that cannot be analyzed with classical methods, and which are based on monitoring peaks of L and L•T only, due to the instability of the target-probe complexes. The NECEEM-based method is superior to ACE-based methods as well because it does not require that the target of interest be a separation buffer component. Along with avoiding target influence on electroosmotic flow it also allows the analysis of extremely small amounts of target. When the probe is fluorescently labeled this application of the invention can quantitate as few as 1000 molecules of T.

Application 3. Selecting Ligands (L) Capable of Binding a Target (T) with Specified $k_n$, $k_{off}$ and $K_d$ The method of the invention in its third application presents a new and powerful approach to select ligands from complex mixtures. Unique capabilities of this method include, but are not limited by: (a) the selection of ligands with specified ranges of $k_{on}$, $k_{off}$ and $K_d$ of target-ligand interactions, (b) the selection of ligands present in minute amounts in complex mixtures of biological or synthetic samples, and (c) the selection of ligands for targets available in very low amounts. The conditions for NECEEM-based screening are chosen such that the components of the sample have similar electrophoretic mobilities and the target has a mobility considerably different from the sample components. Complexes of the target and ligands, which are present in the sample, will have intermediate mobility that can be estimated if the mobilities of the ligands and the target are known. Under such conditions, the sample migrates as a single electrophoretic zone or as a set of close zones and generates a single peak or a set of close peaks. This peak(s) is distinct from the peak of the target. For the simplicity of presentation, hereafter it is assumed that the sample migrates as a single electrophoretic peak (see Example 15).

Figure 3:
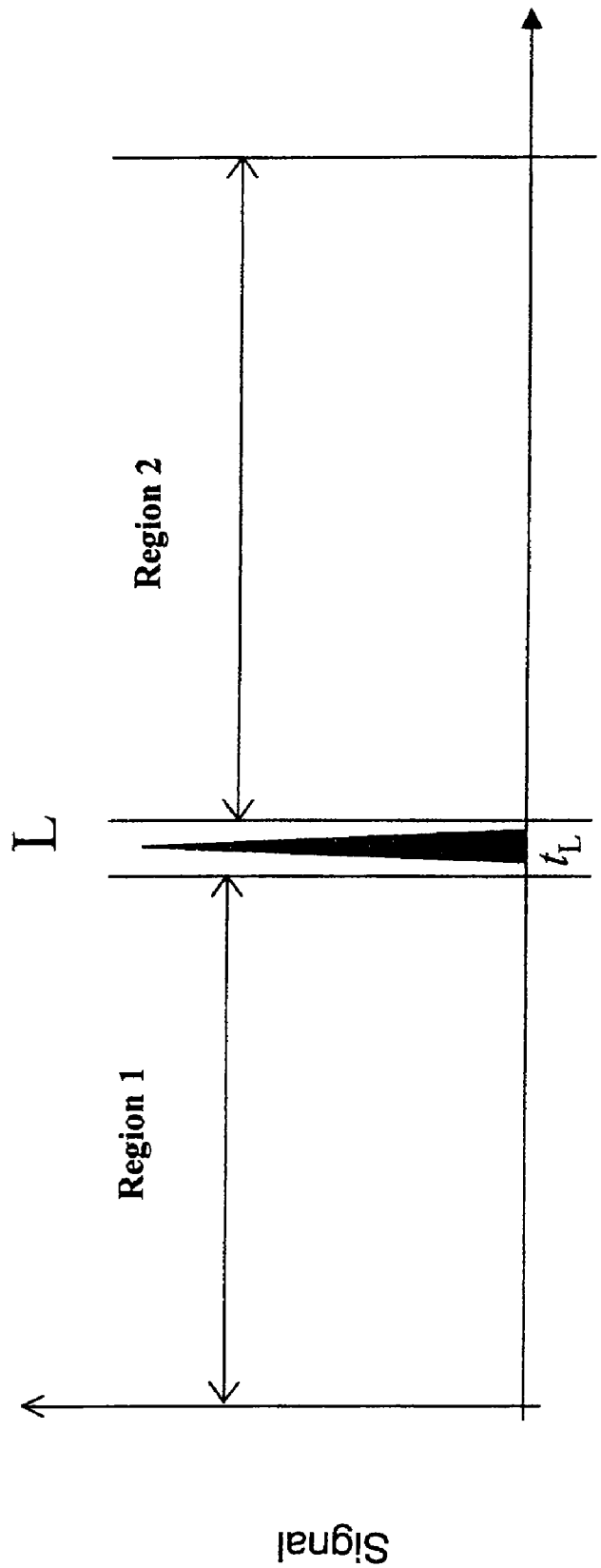
FIG. 3 is a schematic representation of a NECEEM electropherogram during the selection of ligands with $K_d<K_d^{max}=[T]_1$ and $k_{on}>k_{on}^{min}=1/[T]_1t_{eq1}$ when the migration time of the target is unknown. Ligands are selected from both sides of peak L, corresponding to the sample.

In one embodiment, the method of the invention allows for the collecting of a fraction of ligands, capable of binding to the target with ranges of $K_d$ and $k_{on}$, which are defined by the operator, in the following procedure:

1. The ligands are selected with the required upper limit of $K_d$ and lower limit of $k_{on}$. To facilitate this, the mixture of the target (T) and the sample with potential ligands is prepared and equilibrated inside or outside the capillary. If it is prepared outside the capillary, a plug of the mixture is introduced into the capillary. The concentration of the target, $[T]_1$, and the time of mixture equilibration, $t_{eq1}$, are chosen to facilitate the selection of ligands with the required upper limit of $K_d$ and lower limit of $k_{on}$. The upper limit of $K_d$ will be equal to $[T]_1$ while the lower limit of $k_{on}$ will be equal to $1/[T]_1 t_{eq1}$. The ligands with $K_d<[T]_1$ and $k_{on}>[T]_1 t_{eq1}$ will be preferably bound to T, while ligands with $K_d>[T]_1$ or $k_{on}<1/[T]_1 t_{eq1}$ will be preferably in a non-bound state. The mixture is subjected to NECEEM, as described above and the sample is monitored if possible. To this end the components of the sample can be labeled with a tag facilitating detection. For example, if the sample is a combinatorial library of oligonucleotides, all the components can be fluorescently labeled (Example 15). If the target is not detectable by NECEEM, the electropherogram consists of a single peak corresponding to the sample. The target itself may not be detectable either due to its low concentration or due to the lack of a fluorescent (or other) tag. Peaks corresponding to the intact L•T complex and the exponential curve corresponding to its decay, may not be detectable because the concentration of the ligands in the sample may be below the limit of detection. In another embodiment, if the migration time of T is not known, then the ligands within L•T, or formed from the decay of L•T are collected from both sides of peak L (FIG. 3). If the migration time of T is known, then the ligands within L•T, or formed from the decay of L•T are collected in the time window $t_T$-$t_L$ (or $t_L$-$t_T$) from one side of peak L only (FIG. 4). The pool of ligands collected in this way contains selectively the ligands with $K_d<[T]_1$ and $k_{on}>1/[T]_1 t_{eq1}$. The population of ligands with $K_d<[T]_1$ and $k_{on}>1/[T]_1 t_{eq1}$ can be enriched if the fraction collected is subjected to another selection using the same procedure. If the amount of these ligands is not sufficient for further selection, the selection procedure described above can be repeated as many times as required to accumulate the required amount of ligands from the sample. If the ligands are nucleic acids (e.g. oligonucleotide aptamers), they can be amplified in a PCR procedure, instead. The PCR procedure will enrich the population of ligands with $K_d<[T]_1$ and $k_{on}>[T]_1 t_{eq1}$ (see example 15).

Figure 5:
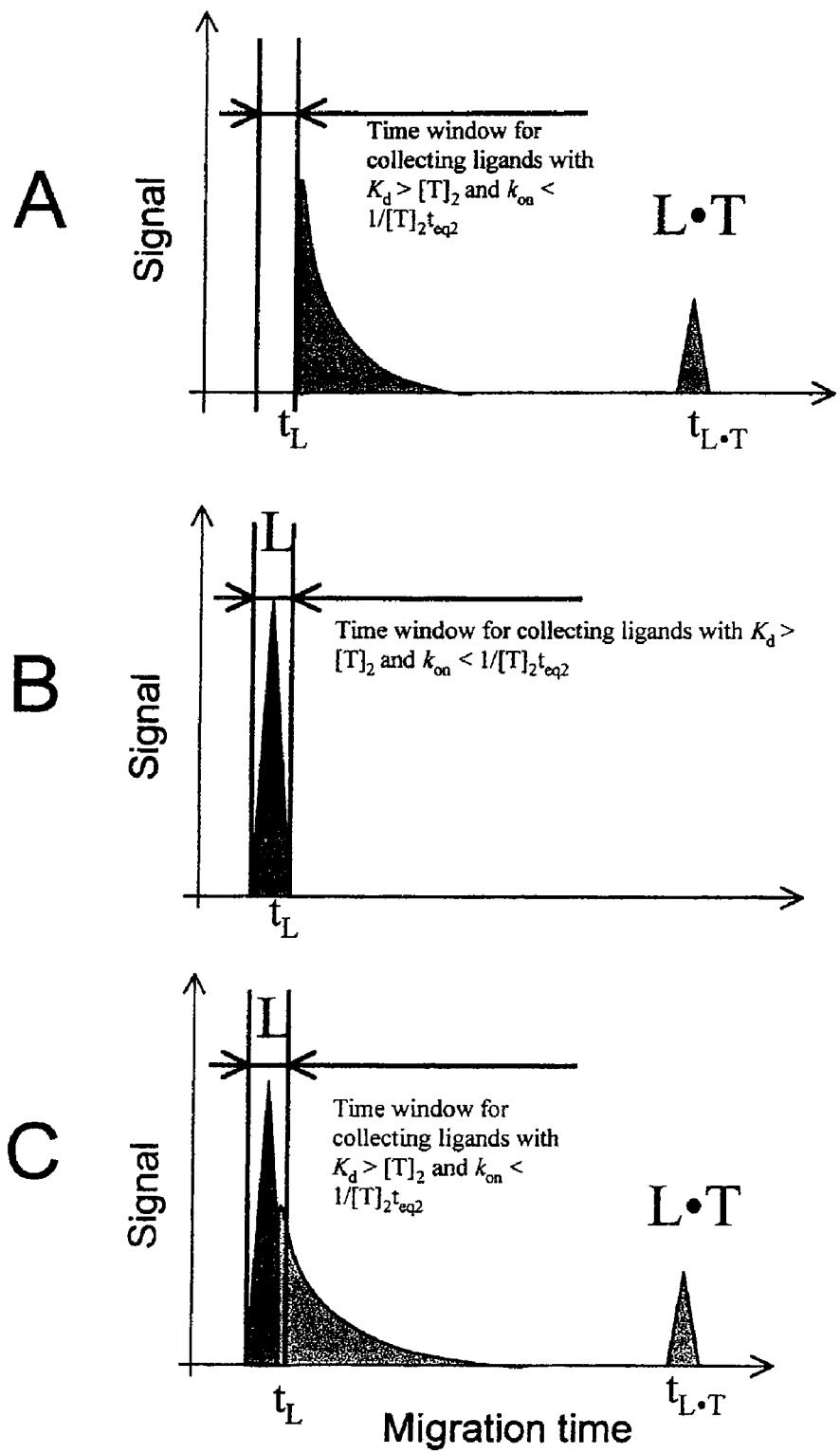
FIG. 5 is a schematic representation of a NECEEM electropherogram during the selection of ligands with $K_d>K_d^{min}=[T]_2$ and $k_{on}<k_{on}^{max}=1/[T]_2t_{eq2}$. Panels A to C demonstrate examples using different values of $[T]_2$ with respect to $[T]_1$, and $t_{eq2}$ with respect to $t_{eq1}$. Panel A illustrates the case when most of the ligands in the pool bind to T and are observed either as peak L•T or its exponential decay. Panel B illustrates the case when little of the fraction of ligands is bound to T so that peak L•T and its decay are not detectable. Panel C illustrates the case when comparable amounts of the ligands bind to T and are present in a non-bound state so that the areas of peak L and peak Da along with its decay are comparable.

2. The ligands with $K_d<[T]_1$ and $k_{on}>1/[T]_1 t_{eq1}$, that have been selected as described in the previous paragraph, are screened to further select ligands with $[T]_2<K_d<[T]_1$ and $1/[T]_2 t_{eq2}>k_{on}>1/[T]_1 t_{eq1}$. To facilitate this, the fraction containing ligands selected in the first round and T, are combined and equilibrated. The concentration of the target, $[T]_2$, and the time of mixture equilibration, $t_{eq2}$, are chosen to facilitate the selection of ligands with the required lower limit of $K_d$ and upper limit of $k_{on}$. The lower limit of $K_d$ will be equal to $[T]_2$ while the upper limit of $k_{on}$ will be equal to $1/[T]_2 t_{eq2}$ where $[T]_2<[T]_1$ and $t_{eq2}<t_{eq1}$. The ligands with $K_d<[T]_2$ and $k_{on}>1/[T]_2 t_{eq2}$ will be preferably bound to T, while ligands with $K_d>[T]_2$ or $k_{on}<1/[T]_2 t_{eq2}$ will be preferably in a non-bound state. The mixture is subjected to NECEEM and the fraction that corresponds to free ligands is collected. Depending on: (i) how different $[T]_2$ is from $[T]_1$ and $t_{eq2}$ is from $t_{eq1}$, and (ii) the total concentration of the ligands in the mixture, different types of NECEEM electropherograms will be observed. First, if $[T]_2$ is close to $[T]_1$ and $t_{eq2}$ is close to $t_{eq1}$, then most of the ligands in the mixture will be bound to T and the peak of free L will not be observed; instead the peak of L•T and the curve corresponding to the decay of L•T will be observed (FIG. 5A). In contrast, if $[T]_2<<[T]_1$ or $t_{eq2}<<t_{eq1}$, then most of the ligands will be in the non-bound state and a single peak of L will be observed (FIG. 5B). There may be a situation when all three features, two peaks and the decay curve, are detectable (FIG. 5C). In any case, the fraction to be collected corresponds to the time window where the peak L is, or would be if it were detectable (see FIGS. 5A, 5B and 5C). The range of $K_d$ and $k_{on}$ values of the selected pool of ligands will narrow as $[T]_2$ approaches $[T]_1$ and $t_{eq2}$ approaches $t_{eq1}$. To enrich for the population of ligands with $[T]_2<K_d<[T]_1$ and $1/[T]_2 t_{eq2}>k_{on}>1/[T]_1 t_{eq1}$ in the pool, the selected ligands are subjected to repetitive procedures of selection. If the amount of collected ligands is not sufficient for further work the procedure can be repeated to accumulate ligands from the sample. If the ligands are nucleic acids (e.g. oligonucleotide aptamers), they can be amplified in a PCR procedure. The values of $K_d$, $k_{on}$, and $k_{off}$ are interconnected through equation 2. Therefore, ligands with $[T]_2<K_d<[T]_1$ and $1/[T]_2 t_{eq2}>k_{on}>1/[T]_1 t_{eq1}$ have a defined range of $k_{off}$: $[T]_1/[T]_2 t_{eq2}>k_{off}>[T]_2/[T]_1 t_{eq1}$. There is a natural limitation for the upper limit of $k_{on}$; the upper limit of $k_{on}$ cannot exceed the diffusion controlled rate constant, which is typically less than $10^{10}$ M$^{-1}$s$^{-1}$.

In another embodiment, the method of the invention advantageously allows for the collection of ligands, capable of binding to the target within a range of $k_{off}$ values as defined by the operator. The mixture of the target and sample, or a pre-selected pool of ligands, is prepared with the concentration of the target that permits binding of most of the ligands. It is advantageous to chose a concentration of T higher than $[T]_1$. The information provided by the decaying complex can be manipulated by a person skilled in the art of CE in several ways, two of which are presented here:

1. It is possible to select the most stable complexes with $k_{off}<k_{off}^{max}$. This can be done by adjusting the migration time of the complex, $t_{L•T}$, so that $t_{L•T}=1/k_{off}^{max}$ and collecting the fraction L•T (FIG. 6A). The value of $t_{L•T}$ can be adjusted by changing the NECEEM separation conditions (within the knowledge of one skilled in the art of CE) such as the length of the capillary, voltage, the composition and pH of the run buffer, etc. If the peak of L•T is not detectable then a fraction is collected blindly in the time window where the peak would be observed if the amount of intact L•T were detectable. If the amount of collected ligands is not sufficient for further work, the procedure can be repeated to accumulate ligands. If the ligands are nucleic acids (e.g. oligonucleotide aptamers), they can be amplified in a PCR procedure.

2. If ligands with $k_{off}^{min} < k_{off} < k_{off}^{max}$ are required, they can be selected by collecting fractions of the decaying complex (FIG. 6B). It is essential in this case to exclude the L•T peak since it contains a pool of ligands with no lower limit of $k_{off}$. The rate of production of L as the complex decays, is described in equation 3. The question to be answered is what is the value of $k_{off}$ of the ligands that are preferably selected if a fraction is collected at time t from the beginning of separation? To answer this question $k_{off}$ has to be found, for which the rate of L formation is maximal at time t. To find this, the following equation has to be solved:

$$\frac{d}{dk_{off}} \frac{d[L]}{dt} = 0 \tag{20}$$

$$\begin{aligned}\frac{d}{dk_{off}} \frac{d[L]}{dt} &= \frac{d}{dk_{off}} \{[L \cdot T]_{eq} k_{off} \exp(-k_{off} t)\} \\ &= [L \cdot T]_{eq} \exp(-k_{off} t) - k_{off} t [L \cdot T]_{eq} \exp(-k_{off} t) \\ &= [L \cdot T]_{eq} \exp(-k_{off} t)(1 - k_{off} t) \\ &= 0\end{aligned}$$

This equation has one solution:

$$K_{off} = 1/t$$

If the fraction is collected in the time window between $t_1$ and $t_2$ (see FIG. 6B), then ligands with $1/t_2 < k_{off} < 1/t_1$ are selected preferably. Because $$\frac{d}{dk_{off}} \frac{d[L]}{dt}$$

is a smooth function of $k_{off}$, ligands with $k_{off} > 1/t_1$ and $k_{off} < 1/t_2$ may also be present in the fraction collected between $t_1$ and $t_2$ even though their selection is less efficient than that of ligands with $1/t_2 < k_{off} < 1/t_1$. The ligand population with desirable $1/t_2 < k_{off} < 1/t_1$ can be enriched if the fraction collected is subjected to another NECEEM procedure with fraction collection within the same time window, $t_1$-$t_2$. If the amount of collected ligands is not sufficient for further work, the procedure of collecting the peak can be repeated to accumulate ligands. If the ligands are nucleic acids, they can be amplified in a PCR procedure.

When selecting for $k_{off}$, the following natural limitation has to be taken into consideration. The maximum possible $k_{on}$ value is the diffusion controlled one, which does not typically exceed $10^{10}$ $M^{-1}s^{-1}$. Using equation 2 the upper limit of the decay constant can be expressed as a function of $K_d$:

$$k_{off} < 10^{10} K_d \tag{22}$$

Thus, $K_d$ of the ligands defines the upper limit of $k_{off}$. For example, if $K_d = 10^{-12}$ M, then $k_{off} < 10^{-2}$ 1/s.

Figure 7:
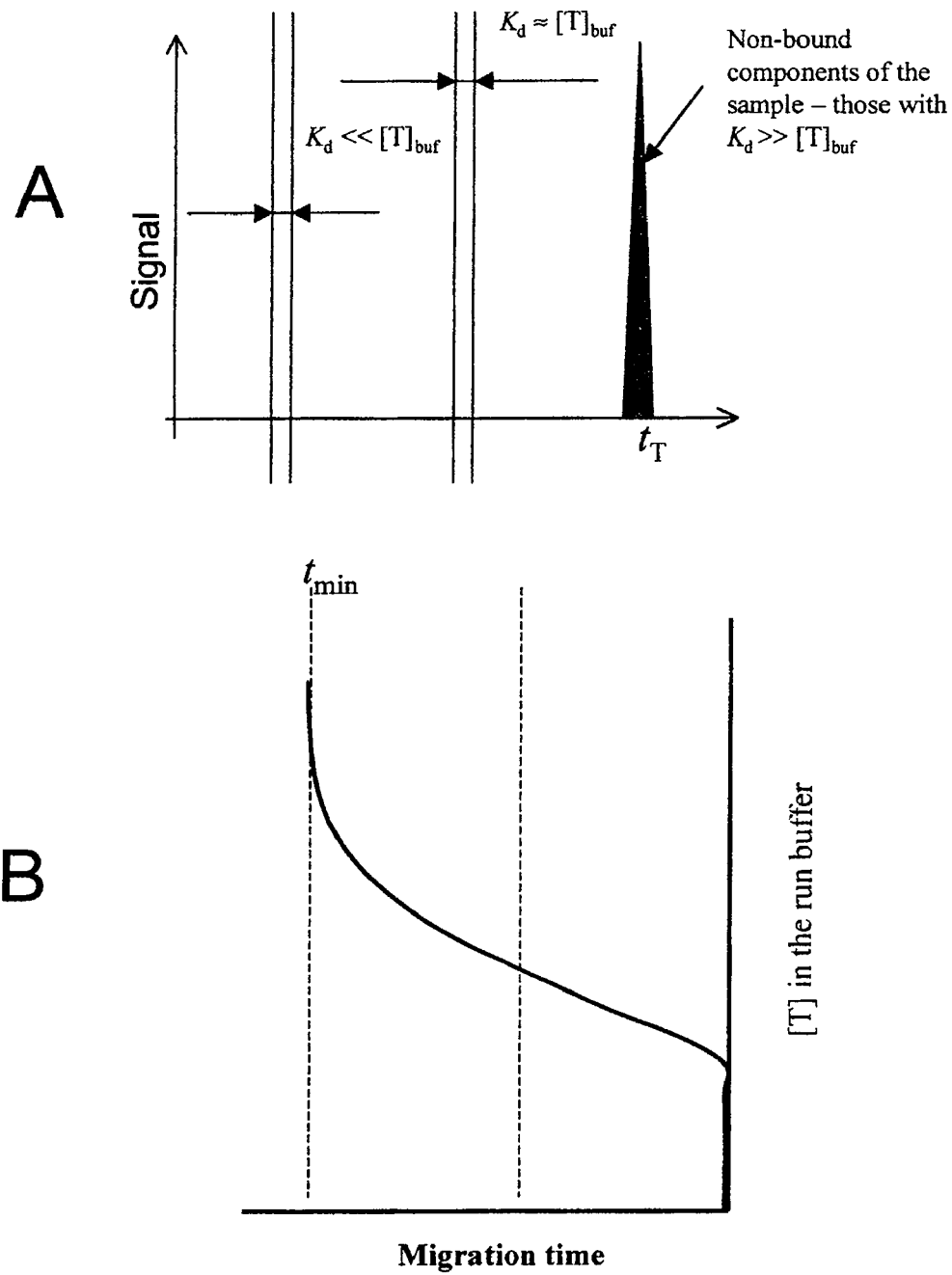
FIG. 7. Panel A schematically represents the electropherogram of a selection of ligands from a sample where the ligands are in very low abundance, using a run buffer that contains the target at concentration $[T]_{buf}$. Panel B represents a schematic Scotchard plot for the ligand with $K_d=[T]_{buf}$.

In another aspect of the method of the invention, the equilibrium mixture is subjected to capillary electrophoresis using a run buffer that contains the target at concentration $[T]_{buf}$. In this case, the ligand-target equilibrium is maintained during the separation. The migration time of different ligands will depend on the $K_d$ values of corresponding ligand-target complexes. If the population of ligands capable of binding the target within the desired $K_d$ range, (comparable to $[T]_{buf}$), is very low, then only the peak corresponding to non-bound components of the sample may be detectable (FIG. 7A). The distribution of the migration times is governed by the Scotchard plot (FIG. 7B). This approach allows the selection of ligands with desired $K_d$ values. This method has the highest accuracy and precision with respect to determining the $K_d$ value of collected ligands when the buffer contains the concentration of the target equal to the value of the desired $K_d$ and the fraction is collected in the middle of the $t_{min}$-$t_T$ time window (see FIG. 7A).

An embodiment of the method of this invention can be applied to a mixture of targets. In this case it facilitates the selection of ligands to multiple targets. If the complexes of these targets with the ligands can be separated, the method can be used to collect individual complexes. The ligands in such complexes can then be identified using other analytical procedures such as a chromatography- or electrophoresis-based affinity analyses. T can be an organic molecule, protein, peptide, enzyme, nucleic acid, aptamer, organelle, cell, virus, particle, or other reagent separable by capillary electrophoresis. L can be any chemical entity than binds the target with required specificity and affinity. L may be a component of the biological sample, patient sample, combinatorial library or other complex mixture. If necessary, T and the sample may be pretreated using different procedures such as, but not limited to: purification, enrichment, fractionation, lysis, freeze-thaw, and centrifugation. Advantageously, the analytical device can be coupled with the capillary electrophoresis instrument. If such a device is a PCR machine, then the procedure for selecting nucleic acid ligands can be automated. If such a device is a mass-spectrometer, then the structure of the ligands can be identified in an "on-line" mode.

To conclude, the method of this invention in its third application advantageously does not require monitoring the shift of the peak of the target. It does not require that the ligands be in detectable amounts—the ligands can be selected "blindly". Furthermore, the method does not require the presence of detectable amounts of target in the equilibrium mixture. This allows for selecting very tight ligands with very low values of $K_d$ (e.g. $K_d < 10^{-9}$ M). The method facilitates repetitive refinement procedures that can lead to a series of ligands with very narrow ranges of $K_d$, $k_{on}$, and $k_{off}$ values or even to a single ligand with desirable $K_d$, $k_{on}$, and $k_{off}$ parameters.

Uses

In general, the method of the invention can be used for discovery and characterization of drug candidates and the development of new diagnostic tools.

The method of this invention will be useful for selecting drug candidates from combinatorial (or other) libraries. Its usefulness is emphasized by its unique ability to select drug candidates with specified values of binding parameters to the therapeutic target. Furthermore, the method of the invention, when performed at different temperatures, will allow the selection of molecules with desirable thermodynamic parameters of binding to the therapeutic target. This unique ability of the method is especially important for developing drugs whose activity is regulated by changing temperatures of the body, such as anti-inflammatory drugs.

The method of the invention will be useful for developing diagnostic probes. Such probes are also subject to the requirements of specific binding parameters between probe and target and the specific dependence of these parameters on temperature. A person with ordinary skills in CE will be able to use the method for the selection of diagnostic probes or drug candidates from different types of combinatorial libraries.

Another exciting application of the method is the selection of aptamers from combinatorial libraries. In particular, the method of this invention is very advantageous for selecting oligonucleotide aptamers for proteins. Oligonucleotide libraries have a unique electrophoretic mobility since oligonucleotides have identical electrophoretic mobilities, independently of their length or hybridization status. Proteins typically have electrophoretic mobility much greater than that of oligonucleotide libraries. Therefore, a protein-aptamer complex typically migrates faster than non-bound oligonucleotides. As a result, non-specific interactions of oligonucleotides with capillary walls do not cause background interference in the selection process. This in turn, allows the method to be used for the selection of aptamers for extremely small amounts of targets. In the first use of the method (see example 15) an aptamer was selected using an amount of target protein, 5 orders of magnitude lower than current state-of-the art methods permit for selection of aptamers (Vant-Hull et al., *J. Mol. Biol.*, 1998, 278, 579).

The method of this invention will be useful for finding binding parameters between drug candidates (developed using other methods) and their therapeutic targets. It will also find use in determining temperature inside channels of microfabricated devices.

The method of this invention will be useful for developing diagnostic a based on CE and aptamers. This method can also be used as a diagnostic tool for the quantification of parameters modified by disease (i.e. altered levels of metabolic products, presence of viral DNA etc.) in patient samples. Many heterogeneous diagnostic methods such as ELISA have unacceptably high levels of false positives due to the limitations discussed above. This invention can provide an alternative to such methods that afford a greater degree of accuracy and sensitivity. Since the method can detect T present in very low concentrations, it may provide enhanced detection of disease markers permitting earlier diagnosis and enhanced treatment options.

The following non-limiting examples are illustrative of the present invention.

EXAMPLES

The following examples are illustrative of preferred embodiments of methods of the invention and are not to be considered as limiting the invention thereto.

Example 1

FIG. 1

Schematic illustration for the determination of $K_d$ and $k_{off}$ values by NECEEM when both L and T are detectable. Panels A, B, and C correspond to low, intermediate and high $k_{off}$ values, respectively.

Panel A. When $k_{off}$ is low, $k_{off} \ll 1/t_{L \cdot T}$, then the complex does not decay during its migration through the capillary. NECEEM then converges into an ordinary equilibrium CE. In an ordinary equilibrium CE, three peaks are observed, corresponding to L, L•T, and T with normalized areas $A_L$, $A_{L \cdot T}$, and $A_T$, respectively. The areas of the peaks represent the equilibrium fractions of L, L•T, and T. The value of $K_d$ can be found using equation 4. In order to determine the value of $k_{off}$, the retention time of L•T in the capillary should be increased to transform the ordinary equilibrium CE into NECEEM. This can be achieved by changing a number of parameters, such as, but not limited to: run buffer components, run buffer ionic strength, run buffer pH, electric filed, and capillary length. Panel B. When $k_{off}$ is intermediate, $k_{off} \sim 1/t_{L \cdot T}$, then the complex experiences a detectable degree of decay during its migration through the capillary. In this case, three peaks are still observed. In addition to the three peaks there are two decay areas, each of which is referred to as $A_{decay}$, corresponding to the fraction of L•T that decayed during the separation. The equilibrium fraction of L•T is represented by the sum area $A_{L \cdot T} + A_{decay}$. The value of $K_d$ can be determined using equation 5. The value of $k_{off}$ can be determined using equations 8-10.

Panel C. When $k_{off}$ is high, $k_{off} \gg 1/t_{L \cdot T}$, then the complex decays so that the intact complex is not detectable. Only two peaks and two decay areas are observed. The equilibrium fraction of L•T is represented by a sole $A_{decay}$ area. The value of $K_d$ can be determined using equation 11. The value of $k_{off}$ can be determined using either of equations 8-9. In order to use equation 10, the retention time of the complex in the capillary must be decreased to allow for detection of the L•T peak. The retention time can be decreased by changing a number of parameters, such as, but not limited to: run buffer components, run buffer ionic strength, run buffer pH, electric filed, and capillary length.

Example 2

FIG. 2

Theoretical illustration for the determination of $K_d$ and $k_{off}$ values by NECEEM when only L is detectable. Panels A, B and C correspond to low, intermediate, and high $k_{off}$ values, respectively.

FIG. 2 schematically exemplifies the important features in a NECEEM electropherogram when only L is detectable (e.g. a fluorescence detector is used and only L has a fluorescent label). A similar approach is applicable when only T is detectable. If only L is detectable, the T peak is not present in the electropherograms. Depending on the values of $k_{off}$ and the migration time, $t_{L \cdot T}$, of the L•T complex, the complex decays to different degrees during its migration through the capillary.

Panel A. If $k_{off} \ll 1/t_{L \cdot T}$ then no detectable decay is observed. NECEEM then converges into an ordinary equilibrium CE. In ordinary equilibrium CE, the electropherogram is comprised of two peaks corresponding to L, and L•T with normalized areas $A_L$, and $A_{L \cdot T}$, respectively. The areas correspond to equilibrium concentrations of L and L•T, $[L]_{eq}$ and $[L \cdot T]_g$, respectively. Thus, a ratio of the two concentrations can be experimentally found:

$$R = \frac{[L]_{eq}}{[L \cdot T]_{eq}} = \frac{A_L}{A_{LT}} \tag{12}$$

and the value of $K_d$ can be calculated according to the following equation:

$$K_d = \frac{[T]_0 (1 + R) - [L]_0}{1 + 1/R} \tag{13}$$

where $[T]_0$ and $[L]_0$ are total concentrations of T and L in the equilibrium mixture. To measure $k_{off}$, the conditions (separation buffer, capillary length, capillary coating, pressure, etc.)

of NECEEM must be changed to increase $t_{L \cdot T}$ to transform the ordinary equilibrium CE into NECEEM.

Panel B. If $k_{off}$ and $1/t_{L \cdot T}$ are of the same order of magnitude, then complex decay is considerable but the peak corresponding to intact L•T is still detectable. The electropherogram in such a case consists of 2 peaks and one decay area. The value of $K_d$ can be found using expression 13 and the following formula for R:

$$R = \frac{[L]_{eq}}{[L \cdot T]_{eq}} = \frac{A_L}{A_{LT} + A_{decay}} \quad (14)$$

where the equilibrium concentration of the complex $[L \cdot T]_{eq}$ is represented by the sum of two areas, $A_{L \cdot T}$ and $A_{decay}$. The value of $k_{off}$ is found by analyzing the decay data. The approaches described above and one of the formulas 6-10 can be used to find $k_{off}$.

Panel C. If $k_{off} \gg 1/t_{L \cdot T}$, then the complex decays to undetectable levels during its migration through the capillary. No peak corresponding to L•T is observed. The electropherogram in such a case consists of 1 peak and 1 decay area. The value of $K_d$ can be found using expression (13) and the following formula for R:

$$R = \frac{[L]_{eq}}{[L \cdot T]_{eq}} = \frac{A_L}{A_{decay}} \quad (15)$$

where the equilibrium concentration of the complex $[L \cdot T]_{eq}$ is represented by a single decay area, $A_{decay}$. The value of $k_{off}$ is found by analyzing the decay data and using one of the equations 6-9. Since the L•T peak is not detectable in this case, the information on the value of $t_{L \cdot T}$ cannot be obtained from NECEEM under these conditions. The NECEEM conditions (separation buffer, capillary coating, pressure etc.) should be changed to shorten the separation time. Alternatively, ACE can be used by a person of ordinary skills in CE to obtain the value of $t_{L \cdot T}$. The value of $K_d$ is associated with the conditions of the equilibrium mixture, and thus is determined by the incubation buffer. The value of $k_{off}$ is associated with the separation conditions, and thus is determined by the separation buffer. If the incubation and separation buffers are the same, then the value of $k_{on}$ can be calculated using expression 2.

Example 3

FIG. 3

Theoretical illustration of using a NECEEM-based method for the selection of ligands with $K_d < K_d^{max} = [T]_1$ and $k_{on} > k_{on}^{min} = 1/[T]_1 t_{eq1}$, when the migration time of the target is unknown.

The ligands are selected with the required upper limit of $K_d$ and lower limit of $k_{on}$. To facilitate this, the mixture of T and the sample, which contains potential ligands, is prepared and equilibrated. The concentration of the target, $[T]_1$, and the time of mixture equilibration, $t_{eq1}$, are chosen to facilitate the selection of ligands with the required upper limit of $K_d$ and lower limit of $k_{on}$. The upper limit of $K_d$ will be equal to $[T]_1$ while the lower limit of $k_{on}$ will be equal to $1/[T]_1 t_{eq1}$. The ligands with $K_d < [T]_1$ and $k_{on} > 1/[T]_1 t_{eq1}$ will be preferably bound to T, while ligands with $K_d > [T]_1$ or $k_{on} < 1/[T]_1 t_{eq1}$ will be preferably in a non-bound state. The mixture is subjected to NECEEM, which works as described above but which may generate a new type of electropherogram consisting of only a single peak. This peak will correspond to the sample components, which do not bind to the target. All the components of the sample may be fluorescently tagged but the target itself may not be detectable either because its concentration is below the limit of detection or because only the sample has been labeled. The peak corresponding to the intact L•T complex and the exponential curve corresponding to its decay may not be detectable because the concentration of the ligands in the sample may be below the limit of detection. If the migration time of T is not known, then the ligands comprising L•T or formed from the decay of L•T are collected from both sides of peak L.

Example 4

FIG. 4

Theoretical illustration of using a NECEEM-based method for the selection of ligands with $K_d < K_d^{max} = [T]_1$ and $k_{on} > k_{on}^{min} = 1/[T]_1 t_{eq1}$, when the migration time of the target is known.

Ligands are collected between $t_T$ and $t_L$ from one side of peak L only: To the left of peak L, if $t_T < t_L$ (Panel A) and to the right of peak L, if $t_T < t_L$ (Panel B).

Example 5

FIG. 5

Schematic representation of a NECEEM electropherogram during the selection of ligands with $K_d > K_d^{min}$ and $k_{on} < k_{on}^{max}$.

Panel A: $[T]_2$ and $t_{eq2}$ are slightly less than $[T]_1$ and $t_{eq1}$, respectively. Most of the ligands in the pool bind to T and are observed either as peak L•T or its exponential decay. No peak of L is detectable. The fraction of ligands is to be collected in the time window where L would be, if it were detectable. The pool of selected ligands will have narrow ranges of $K_d$ (varying from $[T]_2$ to $[T]_1$) and $k_{on}$ (varying from $t_{eq2}$ to $t_{eq1}$).

Panel B: $[T]_2 \ll [T]_1$ or $t_{eq2} \ll t_{eq1}$. Few of the ligands in the pool bind to T. No peak for L•T or its exponential decay are detectable. Instead, only peak L is observed. Peak L is to be collected. The pool of selected ligands will have a large range of $K_d$ (varying from $[T]_2$ to $[T]_1$) or $k_r$ (varying from $t_{eq2}$ to $t_{eq1}$).

Panel C: At least one of $[T]_2$ and $t_{eq2}$ has an intermediate value. The second parameter, $[T]_2$ or $t_{eq2}$, cannot be much less than $[T]_1$ or $t_{eq1}$. A considerable fraction of the ligands bind to T, while a significant fraction do not bind to T. Peaks L and L•T, as well as the exponential decay of L•T, are detectable. Peak L is collected. The pool of selected ligands will have an intermediate range of $K_d$ values (varying from $[T]_2$ to $[T]_1$ or $k_{on}$ values (varying from $t_{eq2}$ to $t_{eq1}$) or both $K_d$ and $k_{on}$ values.

Example 6

FIG. 6

Theoretical illustration using a NECEEM-based method for the selection of ligands with $k_{off} < k_{off}^{max} = 1/t_1$ and $1/t_2 = k_{off}^{min} < k_{off} < k_{off}^{max} = 1/t_1$, where $t_1$ and $t_2$ are time points limiting the time window of fraction selection.

Panel A. To select ligands with $k_{off} < k_{off}^{max}$, a fraction of L•T is collected. The migration time of L•T, $t_{L \cdot T}$, is adjusted by changing the NECEEM conditions to satisfy $t_{L \cdot T} = 1/k_{off}^{max}$.

Panel B. To select ligands with $k_{off}^{min} < k_{off} < k_{off}^{max}$, a fraction of L originating from the decaying complex is collected. The time window of collection, $t_1$-$t_2$, is chosen to satisfy: $t_1 = 1/k_{off}^{max}$ and $t_2 = 1/k_{off}^{min}$. The conditions of NECEEM are adjusted to ensure that $t_{L \cdot T} > t_2$.

Example 7

FIG. 7

Schematic representation of an electropherogram during the selection of ligands from a sample with a very low fraction of ligands, using a run buffer that contains the target at concentration $[T]_{buf}$.

The equilibrium mixture is subjected to capillary electrophoresis using a run buffer that contains the target at concentration $[T]_{buf}$. In this case, the ligand-target equilibrium is maintained during the separation. The migration time of different ligands will depend on the $K_d$ values of corresponding ligand-target complexes. If the population of ligands capable of binding the target with a $K_d$ value comparable to $[T]_{buf}$ is very low, then only the peak corresponding to non-bound components of the sample may be detectable (Panel A). The distribution of the migration times is governed by the Scotchard plot (Panel B). This approach allows selecting ligands with desired $K_d$ values. This method has the highest accuracy and precision with respect to the $K_d$ value of collected ligands when the buffer contains the concentration of the target equal to the value of the desired $K_d$ and the fraction is collected in the middle of the $t_{min}$-$t_T$ time window.

Example 8

FIG. 8

The Determination of Equilibrium and Kinetic Parameters of Complex Formation Between SSB and ssDNA.

SSB and a fluorescently-labeled 15-mer ssDNA oligonucleotide, 5'-fluorescein-GCGGAGCGTGGCAGG (SEQ ID NO: 1) (fDNA) were used in this example (Berezovski and Krylov *J. Amer. Chem. Soc.* 2002, 124, 13674). NECEEM separation of protein-DNA complexes was performed using a laboratory-built CE instrument with fluorescence detector described in detail elsewhere (Wu and Dovichi *J. Chromatogr.* 1989, 480, 141). A 488 nm line of an Argon-ion laser was utilized to excite the fluorescence of the DNA. Uncoated fused silica capillaries of 40 cm×20 μm I.D.×150 μm O.D. were used. The electrophoresis was run with a positive electrode at the injection end biased at +24 kV. The run buffer for NECEEM was 25.0 mM tetraborate at pH 9.4. The samples were injected into the capillary by a pressure pulse of 1 s×9.1 kPa; the length of corresponding sample plug was 0.93 mm as was calculated using the Poiseulle equation (Krylov et al. *Anal. Chem.* 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

Figure 8:
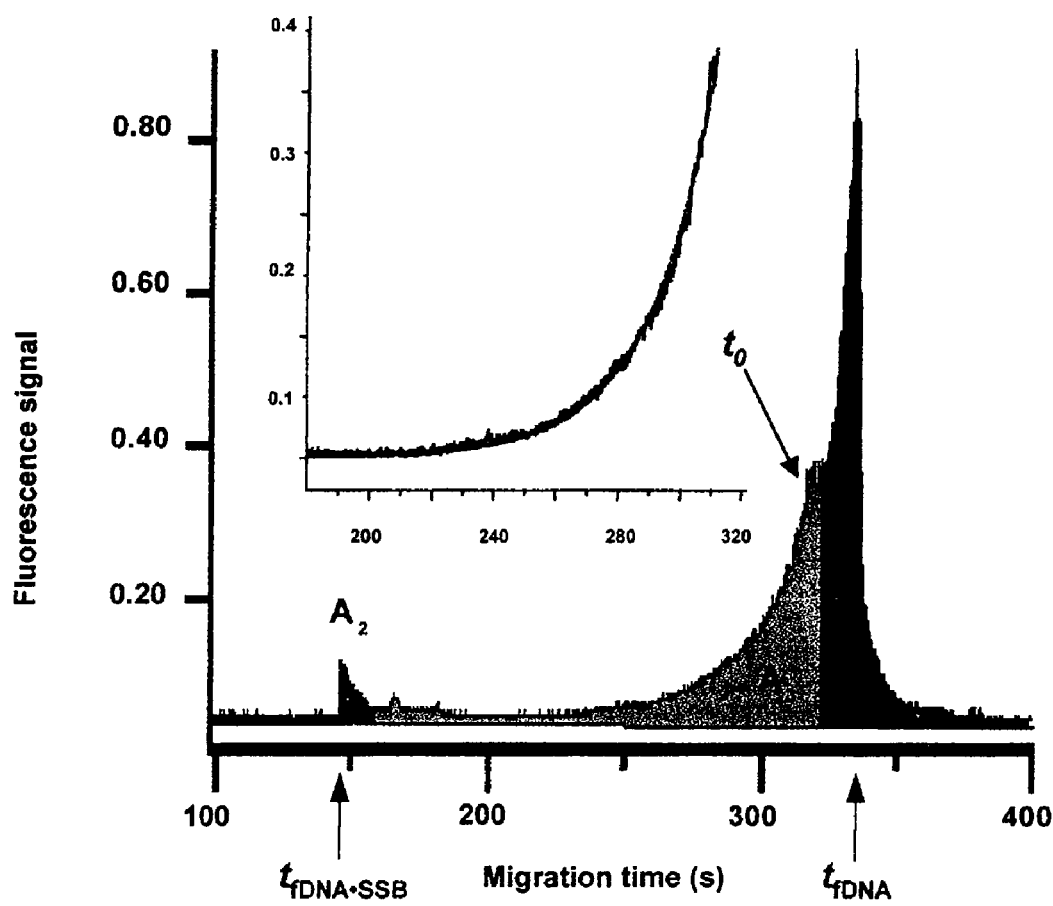
FIG. 8 depicts the use of a NECEEM-based method for determining the $K_d$, $k_{off}$, and $k_{on}$ values of complex formation between an SSB protein and a fluorescently labeled 15-mer oligonucleotide, 5'-fluorescein-GCGGAGCGTGGCAGG (SEQ ID NO:1) (fDNA). The total concentrations of the components in the equilibrium mixture are: $[SSB]_0=0.32$ µM and $[fDNA]_0=0.16$ µM. The run buffer was 25.0 mM borate at pH 9.4. The inset illustrates the fitting of the exponential part with a single-exponential function.

Equilibrium mixtures of SSB, fDNA and SSB•fDNA complex were prepared by mixing solutions of 16 μM SSB and 205 nM fDNA in the run buffer at a desired volume ratio and incubating them at room temperature to reach equilibrium prior to the analysis. Equilibrium mixtures contained three components: free SSB, free fDNA and the fDNA•SSB complex. FIG. 8 shows that NECEEM separation of such mixtures generated electropherograms with three essential features: peak 1 (with area $A_1$) corresponding to free fDNA, peak 2 (with area $A_2$) corresponding to the ssDNA•SSB complex that remained intact at the time it passed the detector, and exponential curve 3 (with area $A_3$) corresponding to the decay of fDNA•SSB during the separation. The areas were determined and the value of $K_d$ was calculated using equation 13, $K_d = 2.8 \times 10^{-7}$ M.

The exponential curve was fitted with a single-exponential function 6 and the value of $k_{off}$ was determined, $k_{off} = 3.3 \times 10^{-2}$ s$^{-1}$. The value of $k_{on}$ was then calculated using equation 2, $k_{on} = 1.2 \times 10^5$ M$^{-1}$ s$^{-1}$.

Example 9

FIG. 9

The Determination of Equilibrium and Kinetic Parameters of Complex Formation Between the Mef2c Protein and dsDNA.

Mef2c DNA-binding protein and its dsDNA target were used in this example. The target dsDNA was a total of 26 base pairs including the 10 base pair-long sequence, GATTTT-TATT (SEQ ID NO: 6), binding site of Mef2c. The dsDNA was labeled with fluorescein. NECEEM separation of protein-DNA complexes was performed using a commercial P/ACE MDQ apparatus (Beckman-Coulter) with fluorescence detection. A 488 nm line of an Argon-ion laser was utilized to excite the fluorescence of the dsDNA. Uncoated fused silica capillaries of 40 cm×20 μm I.D.×375 μm O.D. were used. Electrophoresis was carried out with a positive electrode at the injection end biased at +16 kV. The run buffer used for NECEEM was 25.0 mM tetraborate at pH 9.4. The samples were injected into the capillary by a pressure pulse of 5 s×5 psi; the length of corresponding sample plug was 4 mm as was calculated using the Poiseulle equation (Krylov et al. *Anal. Chem.* 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

Figure 9:
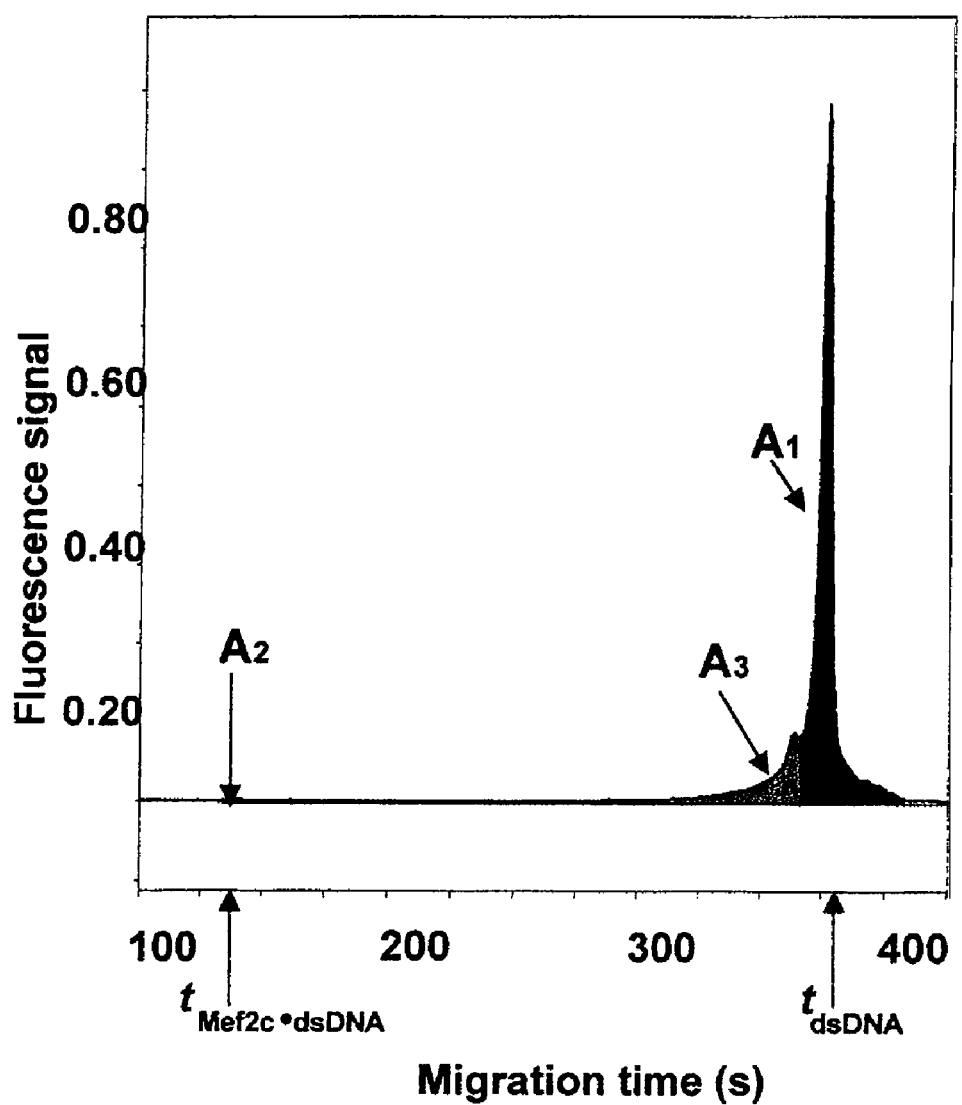
FIG. 9 illustrates the use of a NECEEM-based method for determining the $K_d$, $k_{off}$, and $k_{on}$ values of complex formation between the Mef2c protein and a fluorescently labeled dsDNA of the following sequence: CCTGCCACGCTC-CGCTCTAAAAATAA (SEQ ID NO:2). The total concentrations of the components in the equilibrium mixture were: $[Mef2c]_0=1.0$ µM and $[dsDNA]_0=0.1$ µM. The run buffer was 25.0 mM tetraborate at pH 9.4.

Equilibrium mixtures of Mef2c, dsDNA and Mef2c•dsDNA complex were prepared by mixing Mef2c (1.0 μM) and dsDNA (100 nM) in the run buffer, and incubating them at room temperature to reach equilibrium prior to the analysis. Equilibrium mixtures contained three components: free Mef2c, free dsDNA and the Mef2c•dsDNA complex. FIG. 9 shows the NECEEM separation of such mixtures generated electropherograms with three essential features: peak 1 (with area $A_1$) corresponding to free dsDNA, peak 2 (with area $A_2$) corresponding to the Mef2c•dsDNA complex that remained intact at the time of passing the detector and exponential curve 3 (with area $A_3$) corresponding to the decay of the Mef2c•dsDNA complex during separation. The areas were determined and the values of $K_d$ and $k_{off}$ were calculated using equations 13 and 10, respectively: $K_d = 4.8 \times 10^{-4}$ M, $k_{off} = 0.022$ s$^{-1}$. The value of $k_{on}$ was then calculated using equation 2: $k_{on} = 45$ M$^{-1}$ s$^{-1}$. NECEEM allowed the determination of binding parameters of Mef2c with its dsDNA target for the first time.

Example 10

FIG. 10

Determination of Equilibrium and Kinetic Parameters of Complex Formation Between DNA Polymerase and its Aptamer.

Taq DNA polymerase and its dsDNA aptamer (Yakimovich et al. Biochemistry, Moscow, 2003, 68, 228) were used in this example. The aptamer was fluorescently-labeled with a 15-mer oligonucleotide, 5'-fluorescein-GCGGAGCGTG-GCAGG SEQ ID NO: 1) (fDNA). To facilitate this kind of labeling, the aptamer was extended with a strand of DNA complementary to the fDNA. FDNA formed a hybridization complex with the DNA extension on the aptamer. The labeling procedure involved simply mixing the extended aptamer with the fDNA. Since it is impossible to ensure an ideal 1:1 ratio between the aptamer and fDNA while mixing, one of the components is present in excess and can be separated from the other.

NECEEM of protein-DNA complexes was performed using a commercial P/ACE MDQ apparatus (Beckman-Coulter) with fluorescence detection. A 488 nm line of an Argon-ion laser was utilized to excite the fluorescence of the labeled aptamer. Uncoated fused silica capillaries of 40 cm×75 μm I.D.×375 μm O.D. were used. Electrophoresis was carried out with a positive electrode at the injection end biased at +16 kV. The run buffer used for NECEEM contained 100 nM SSB in 25.0 mM tetraborate at pH 9.4 (SSB in the run buffer was needed to separate the excess of fDNA from the aptamer). The samples were injected into the capillary by a pressure pulse of 5 s×0.5 psi; the length of corresponding sample plug was 5 mm as was calculated using the Poiseulle equation (Krylov et al. *Anal. Chem.* 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

Figure 10:
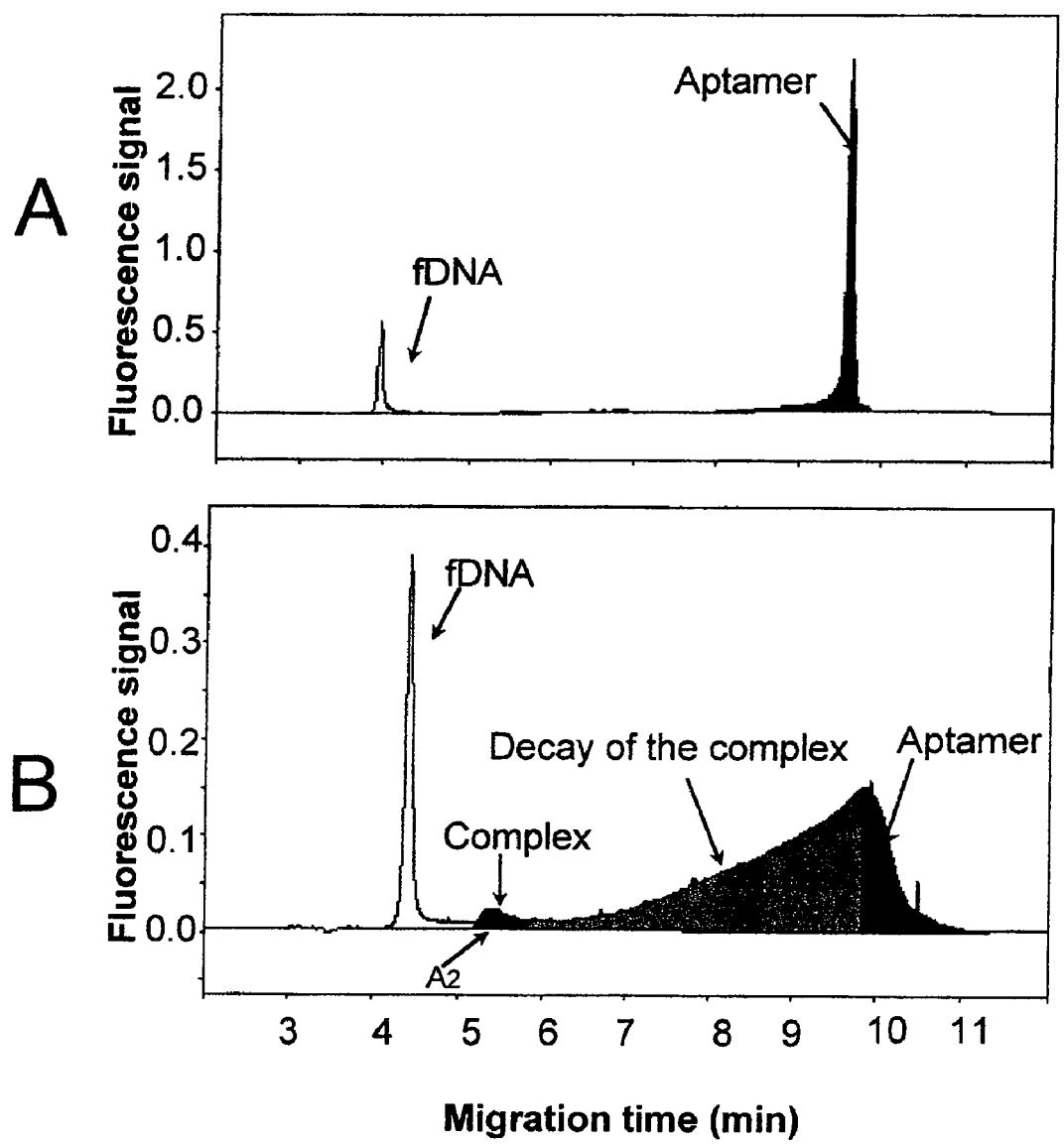
FIG. 10 illustrates the use of a NECEEM-based method for determining the $K_d$, $k_{off}$, and $k_{on}$ values of complex formation between Taq DNA polymerase and its fluorescently labeled aptamer. Panel A shows the separation of excess fDNA from the aptamer-fDNA hybrid. Panel B illustrates a NECEEM electropherogram for the Taq DNA polymerase•aptamer complex. The total concentrations of the components in the equilibrium mixture were: [Taq DNA polymerase]$_0$=5 nM and [Aptamer]$_0$=50 nM. The run buffer contained 100 nM SSB in 25.0 mM tetraborate at pH 9.4.

Equilibrium mixtures of Taq DNA polymerase, its aptamer and the complex of the protein and aptamer, were prepared by mixing solutions of 50 nM Taq DNA polymerase and 100 nM aptamer in the run buffer, at a desired volume ratio and incubating them at room temperature to reach equilibrium, prior to the analysis. Equilibrium mixtures contained four components: free Taq DNA polymerase, free aptamer, the Taq DNA polymerase•aptamer complex and excess fDNA. FIG. 10 shows that NECEEM separation of such mixtures generated electropherograms with four essential features: peak 1 (with area $A_1$) corresponding to free aptamer, peak 2 (with area $A_2$) corresponding to the Taq DNA polymerase•aptamer complex that remained intact by the time of its passing the detector and exponential curve 3 (with area A3) corresponding to the decay of the Taq DNA polymerase•aptamer complex during the separation, and excess fDNA. The areas were determined and the values of $K_d$ and $k_{off}$ were calculated: $K_d$=1.35×10$^{-9}$ M and $k_{off}$=0.01 s$^{-1}$. The value of $k_{on}$ was then calculated using the follow equation, $k_{on}$=7.4×10$^6$ M$^{-1}$ s$^{-1}$.

Example 11

FIG. 11

The Use of a DNA-Binding Protein as an Enhancer of Separation of ssDNA from dsDNA in the Determination of Equilibrium and Kinetic Parameters of a DNA Hybridization Complex Formation.

To use NECEEM in studies of binding parameters of DNA hybridization reactions, ssDNA has to be separated from the dsDNA hybrid. Electrophoretic mobilities of ssDNA and dsDNA are similar in a gel-free electrophoresis buffer. Therefore, ssDNA cannot be readily separated from dsDNA in such a media. Using gel in NECEEM may not be practical as it increases the separation time. Here, it is demonstrated that SSB can facilitate efficient separation of ssDNA from dsDNA in a gel-free buffer. This tool is used in the NECEEM study of kinetic and equilibrium parameters of DNA hybridization reactions.

NECEEM analyses were performed using a commercial P/ACE MDQ apparatus (Beckman-Coulter) with fluorescence detection. A 488 nm line of an Argon-ion laser was utilized to excite the fluorescence of the fluorescently labeled DNA. Uncoated fused silica capillaries of 40 cm×20 μm I.D.×375 μm O.D. were used. The distance from the injection end to the detector was 30 cm. Electrophoresis was run with a positive electrode at the injection end biased at +16 kV (400 V/cm). The run buffer used for NECEEM was 25.0 mM tetraborate at pH 9.4 supplemented with 100 nM SSB protein. The samples were injected into the capillary by a pressure pulse of 5 s×5 psi; the length of corresponding sample plug was 4 mm as was calculated using the Poiseulle equation (Krylov et al. *Anal. Chem.* 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

Figure 11:
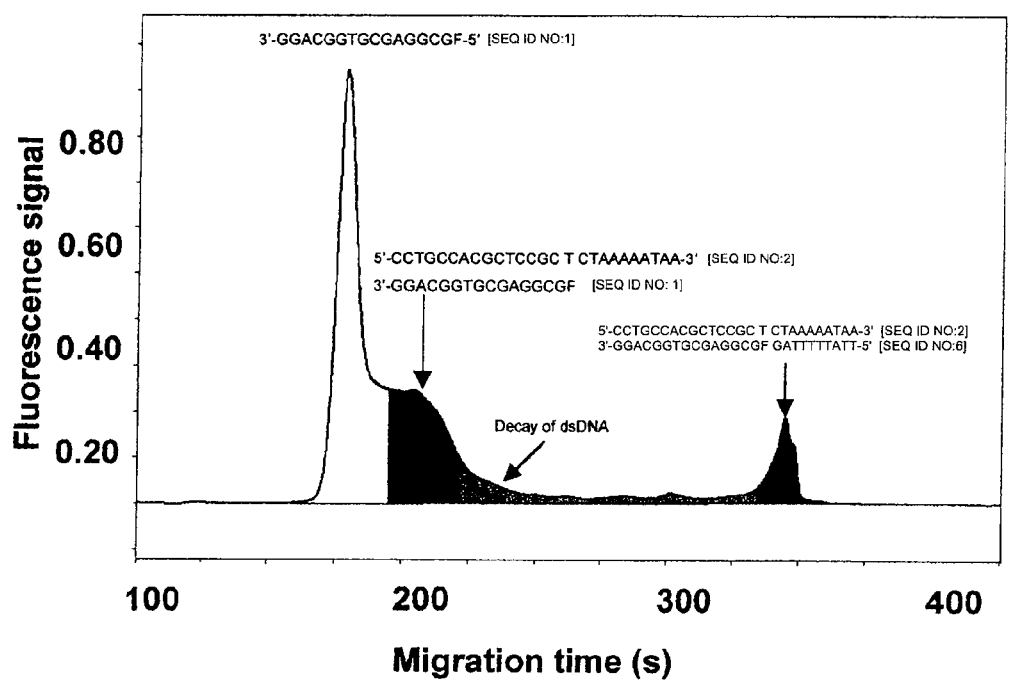
FIG. 11 depicts the use of a DNA-binding protein, SSB, in a NECEEM-based method for determining the $K_d$, $k_{off}$, and $k_{on}$, values of complex formation. SSB enhances separation of ssDNA from dsDNA, aiding in the determination of equilibrium and kinetic parameters of DNA hybridization complex formation (SEQ ID NOS: 1, 2 and 5).
Figure 12:
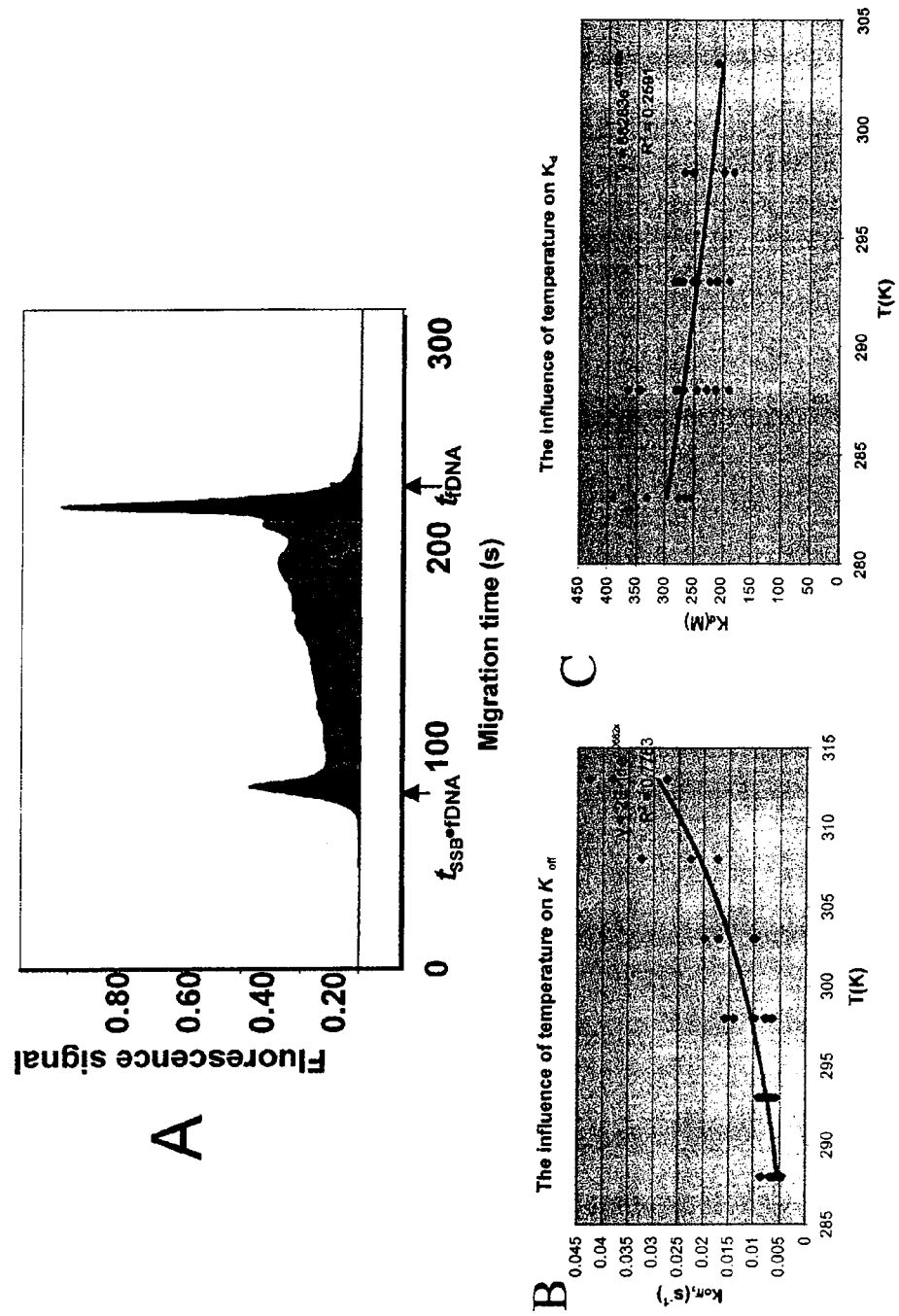
FIG. 12 illustrates the use of a NECEEM-based method for determining thermodynamic parameters of complex formation between SSB and fDNA. Panel A is a typical NECEEM electropherogram. Panel B illustrates the dependence of $k_{off}$ on temperature while Panel C illustrates the dependence of $K_d$ on temperature.

In this example, binding parameters of the hybridization complex were determined between two 10 base-pair long complementary strands of the following sequence: GATTTT-TATT (SEQ ID NO: 6). To demonstrate the power of the proposed method a rather complex equilibrium mixture was designed. It was prepared by mixing three solutions: (i) 200 nM 5'-fluorescein-GCGGAGCGTGGCAGG (SEQ ID NO: 1) (DNA-1), (ii) 200 nM 5'-TTATTTTTAG (SEQ ID NO: 3) (DNA-2), and 100 nM 5'-CCTGCCACGCTC-CGCTCTAAAAATAA (SEQ ID NO: 2) (DNA-3) and incubating them at room temperature to reach equilibrium prior to analysis. DNA-1 and DNA-2 formed a hybrid with DNA-3 (FIG. 11). The total concentrations of DNA-1 and DNA-2 were 200 nM while that of DNA-3 was 100 nM. The equilibrium mixture contained six components: three single stranded DNA molecules (DNA-1, DNA-2, DNA-3) and three complexes (DNA-1•DNA-3, DNA-2•DNA-3, and DNA-1•DNA-3•DNA-2). Only DNA-1 was fluorescently labeled; thus only the following components were detectable: DNA-1, DNA-1•DNA-3, and DNA-1•DNA-3•DNA-2.

When NECEEM was conducted using a run buffer lacking SSB, a single peak was observed—the components of the equilibrium mixture could not be separated without SSB. In the SSB-containing run buffer experiment, a typical NECEEM electropherogram was observed (see FIG. 11). The equilibrium fraction of DNA-1, which was SSB-bound-ssDNA, migrated faster than all other components. It generated the peak with the shortest migration time. The DNA-1•DNA-3 complex had a 10-base-pair-long overhang of ssDNA that could also bind SSB. The DNA-1•DNA-3 complex generated a shoulder to the peak of DNA-1. DNA-1•DNA-3•DNA-2 was dsDNA with no single-stranded overhangs; thus it did not bind SSB and migrated much slower than DNA-1 and DNA-1•DNA-3. It generated the peak with the longest migration time. During its separation, DNA-1•DNA-3•DNA-2, experienced decay—DNA-2 was dissociating from DNA-1•DNA-3•DNA-2 and generated a typical single-exponential decay trace. The value of $k_{off}$=3×10$^{-3}$ s$^{-1}$ was calculated from the areas using equation 10. The value of $K_d$ was found to be 2.7×10$^{-7}$ M from equation 13. The value of $k_{on}$ was then calculated from equation 2 as 1.1×10$^4$ M$^{-1}$ s$^{-1}$.

Example 12

FIG. 12

Determination of Thermodynamic Parameters of Complex Formation Between SSB and a 15-mer Oligonucleotide.

In this example NECEEM was used to determine the activation energy of forward and reverse reactions, reaction enthalpy as well as the change of entropy. SSB and fDNA were used in this example. NECEEM separation of SSB•fDNA complexes was performed using a commercial P/ACE MDQ apparatus (Beckman-Coulter) with fluorescence detection. A 488 nm line of an Argon-ion laser was utilized to excite the fluorescence of the fDNA. Uncoated fused silica capillaries of 40 cm×20 µm I.D.×375 µm O.D. were used. Electrophoresis was carried out with a positive electrode at the injection end biased at +16 kV. The run buffer for NECEEM was 25.0 mM tetraborate at pH 9.4. The samples were injected into the capillary by a pressure pulse of 5 s×5 psi; the length of corresponding sample plug was 4 mm as was calculated using the Poiseulle equation (Krylov et al. Anal. Chem. 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

Equilibrium mixtures of SSB, fDNA and SSB•fDNA complex were prepared by mixing solutions of 16 µM SSB and 205 nM fDNA in the run buffer at a desired volume ratio. The equilibrium mixtures were incubated at different temperatures and electrophoretic runs were carried out at different temperatures of the capillary. The areas of electrophoretic features were determined and the values of $K_d$, $k_{off}$, and $k_{on}$, were calculated as depicted in Panel A, using equations 13, 14, 10 and 2. The values of $K_d$ and $k_{off}$ were plotted as functions of temperature as shown in Panels B and C. Thermodynamic parameters, $E_{a(off)}$, $E_{a(on)}$, $\Delta H°$, and $\Delta S°$ were then calculated using equations 16-18:

$$E_{a(on)} = E_{a(off)} - \Delta H°$$
$$= 63. \text{ kJ/mol}$$

$$\ln k_{off} = -\frac{E_{a(off)}}{R} \frac{1}{T}$$

$$E_{a(off)}R = \text{slope}$$

$$E_{a(off)} = \text{slope} \times R = 6.0 \times 10^3 \times 8.314 \approx 50. \text{kJ/mol}$$

$$\ln K_d = -(\Delta H° - T\Delta S°)/RT = -\Delta H°/RT + \Delta S°/R$$

$$\Delta H° = -\text{slope} \times R = -1.6 \times 10^3 \times 8.314 = -13. \text{kJ/mol}$$

$$\Delta S° = \text{intercept} \times R = 7.6 \times 10^{-2} \times 8.314 = 0.63 \text{ J/mol} \times K$$

Example 13

FIG. 8

Determination of Temperature Inside a Capillary during Electrophoresis using Temperature-Dependence of Thermodynamic Parameters of Complex Formation between SSB and fDNA.

In this example a CE instrument lacking capillary thermo-stabilization was used. The goal of this example was to determine the temperature inside the capillary during electrophoresis. For this, thermodynamic data obtained in example 12 (using a CE instrument with thermo-stabilized capillary) and the $K_d$ value obtained in this example under conditions of unknown inner capillary temperature, were used.

The temperature dependence of complex formation parameters for SSB and fDNA were used in this example to determine the unknown temperature inside the capillary. NECEEM separation of SSB•fDNA complexes was performed using a laboratory-built CE instrument with fluorescence detector described in detail elsewhere (Wu and Dovichi J. Chromatogr. 1989, 480, 141). A 488 nm line of an Argon-ion laser was utilized to excite the fluorescence of the fDNA. Uncoated fused silica capillaries of 40 cm×20 µm I.D.×150 µm O.D. were used. Electrophoresis was run with a positive electrode at the injection end biased at +16 kV. The run buffer for NECEEM was 25.0 mM tetraborate at pH 9.4. The samples were injected into the capillary by a pressure pulse of 1 s×9.1 kPa; the length of corresponding sample plug was 0.93 mm as was calculated using the Poiseulle equation (Krylov et al. Anal. Chem. 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

The NECEEM electropherograms obtained are identical to those depicted in FIG. 8. Therefore, this example is not accompanied by a graphic illustration. Using thermodynamic parameters, $\Delta H°$ and $\Delta S°$, determined in example 12, and $K_d$ determined in this experiment, the temperature inside of the capillary was calculated with the following equation:

$$T = \frac{\Delta H°}{R(\Delta S°R - \ln K_d)}$$

The temperature inside the non-thermo-stabilized capillary was found to be 35° C., that is 15° C. higher than the ambient temperature of 20° C. Using this method, the temperature can be determined in channels of non-thermo-stabilized microfabricated devices.

Example 14

FIG. 13

Determination of Unknown Concentration of Thrombin using its Aptamer.

In this example the use of a NECEEM-based method for the determination of an unknown concentration of thrombin (T) using its aptamer, (L), is demonstrated (Berezovski et al. Anal. Chem. 2003, 75, 1392). The aptamer was fluorescently-labeled with fDNA. To facilitate this kind of labeling, the aptamer was extended with a strand of DNA complementary to the fDNA. FDNA formed a hybridization complex with the DNA extension on the aptamer. The labeling procedure involved simply mixing the extended aptamer with the fDNA. Since it is impossible to ensure an ideal 1:1 ratio between the aptamer and fDNA while mixing, one of the components is present in excess and can be separated from the other.

NECEEM analysis of the thrombin•aptamer complex was performed using a commercial P/ACE MDQ apparatus (Beckman-Coulter) with fluorescence detection. A 488 nm line of an Argon-ion laser was utilized to excite the fluorescence of the fDNA. Uncoated fused silica capillaries of 40 cm×20 µm I.D.×375 µm O.D. were used. Electrophoresis was carried out with a positive electrode at the injection end biased at +16 kV. The run buffer for NECEEM was 25.0 mM tetraborate supplemented with 100 nM SSB at pH 9.4. SSB served to enhance the separation of L from L•T. The samples were injected into the capillary by a pressure pulse of 5 s×5 psi; the length of corresponding sample plug was 4 mm as was calculated using the Poiseulle equation (Krylov et al. *Anal. Chem.* 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

Figure 13:
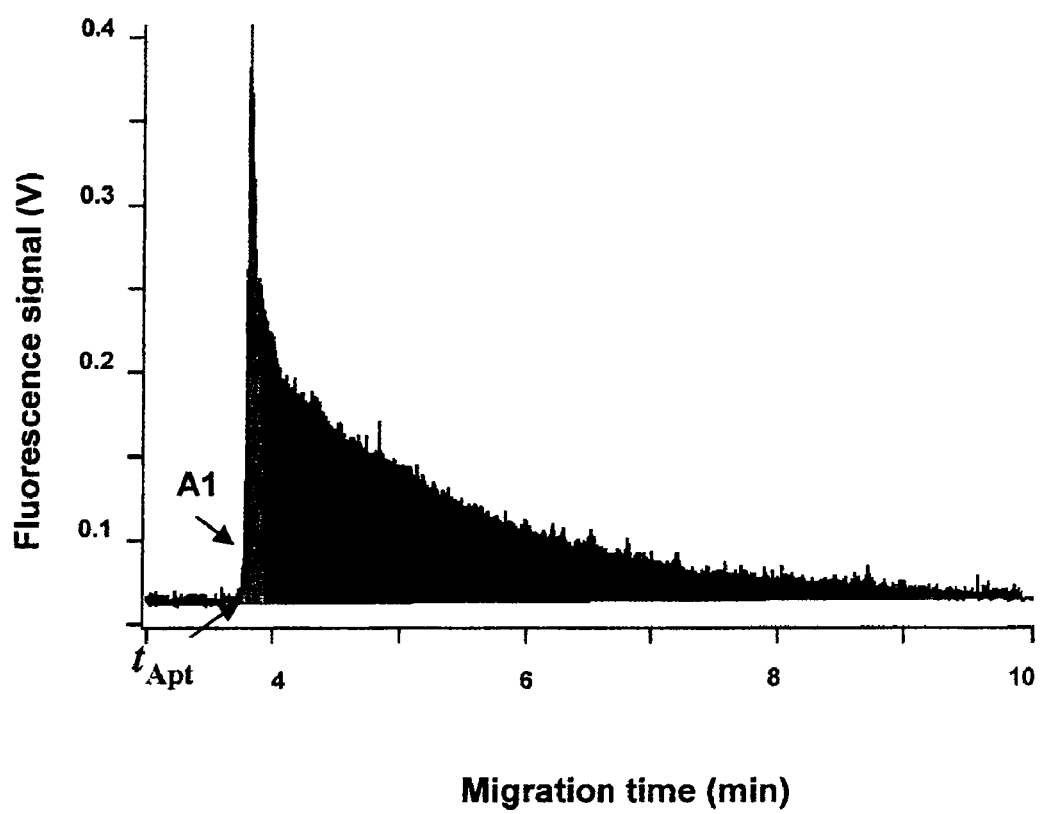
FIG. 13 illustrates the use of a NECEEM-based method for determining an unknown concentration of thrombin using its aptamer.

First, the $K_d$ value of the thrombin•aptamer complex was determined using known concentrations of T and L by way of the approach described in examples 2, 8, 9, and 10. The $K_d$ value was found to be $2.4 \times 10^{-7}$ M. Then, an unknown concentration of T was determined in a blind experiment. For this, the equilibrium mixture containing the unknown concentration of T and known concentration of L was prepared and subjected to NECEEM. The areas under the peak and curve, $A_1$ and $A_2$, (see FIG. 13) were determined and equation 19 was used to calculate the unknown concentration of thrombin.

The relative standard deviation of the method was 15%. The concentration and mass limits of detection for thrombin quantitation were found to be 60 nM and $7 \times 10^6$ molecules, respectively. The dynamic range of the method was two orders of magnitude of thrombin concentration at a fixed aptamer concentration of 61 nM.

Example 15

FIGS. 14-16

Selection of an Aptamer to PFTase from a Combinatorial Library of Oligonucleotides.

PFTase was used as a target to create aptamers from a combinatorial library of DNA oligonucleotides.

The combinatorial library of DNA oligonucleotides was purchased from IDT Technologies and contained two constant parts (16-mer and 20-mer) and one random part (35-mer with equal probability of all four nucleotides A, T, C, and G): 5'-CCT GCC ACG CTC CGC TNN NNN NNN NNN NNN NNN NNN NNN NNN NNN NNN NNN TTC GAC ATG AGG CCC GGA TC-3' (SEQ ID NO: 4), where N represents a random nucleotide. All oligonucleotides in the library were fluorescently labeled by annealing the 16-mer constant part with a complementary 15-mer oligonucleotide labeled with fluorescein (fDNA).

NECEEM separation of protein•DNA complexes was performed using a commercial P/ACE MDQ apparatus (Beckman-Coulter) with fluorescence detection. A 488 nm line of an Argon-ion laser was utilized to excite the fluorescence of the fDNA. Uncoated fused silica capillaries of 40 cm×75 μm I.D.×375 μm O.D. were used. The distance from the injection end to the detector was 30 cm. Electrophoresis was run with a positive electrode at the injection end biased at +16 kV (400 V/cm). The run buffer used for NECEEM was 25.0 mM tetraborate at pH 9.4. The samples were injected into the capillary by a pressure pulse of 5 s×0.5 psi; the length of corresponding sample plug was 5 mm as was calculated using the Poiseulle equation (Krylov et al. *Anal. Chem.* 2000, 72, 872). The capillary was rinsed with the run buffer solution for 2 minutes prior to each run. At the end of each run, the capillary was rinsed with 100 mM NaOH for 2 minutes, followed by a rinse with deionized water for 2 minutes.

Figure 14:
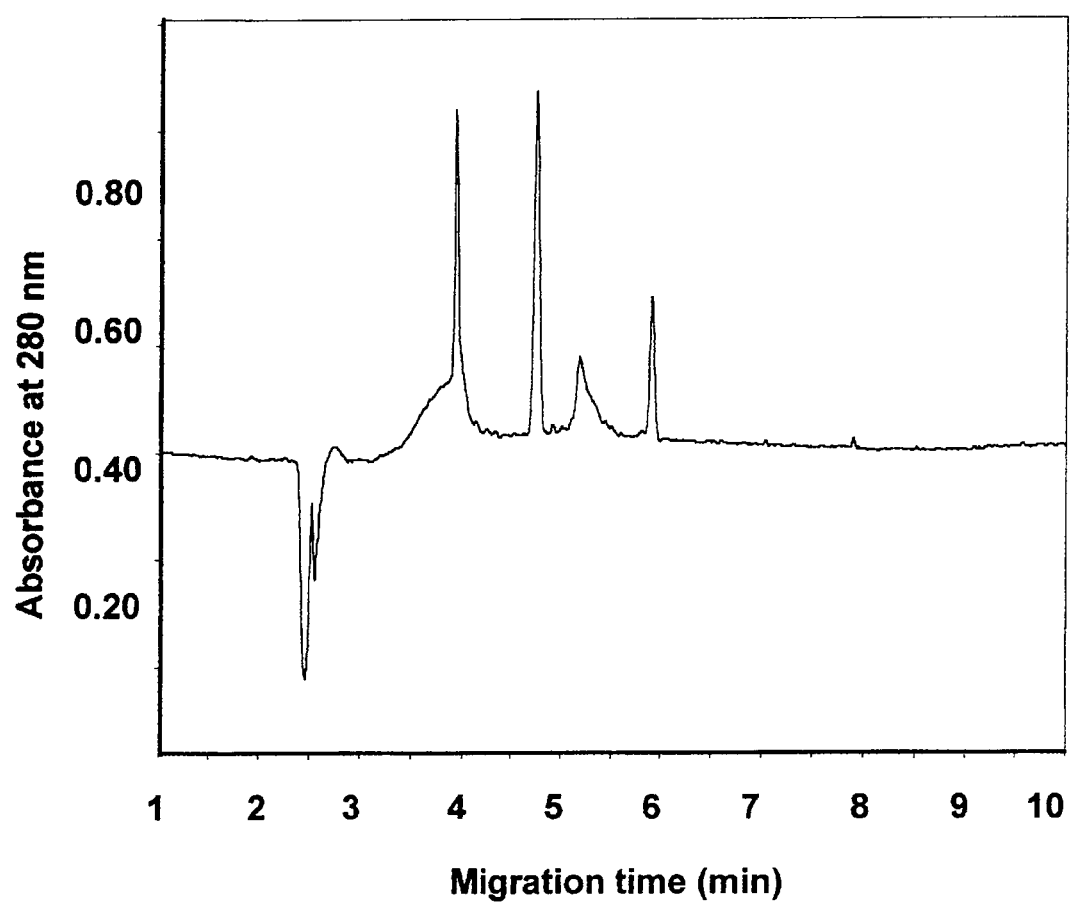
FIG. 14 shows a capillary electrophoresis of 1 µM PFTase detected using light absorption at 280 nm.
Figure 15:
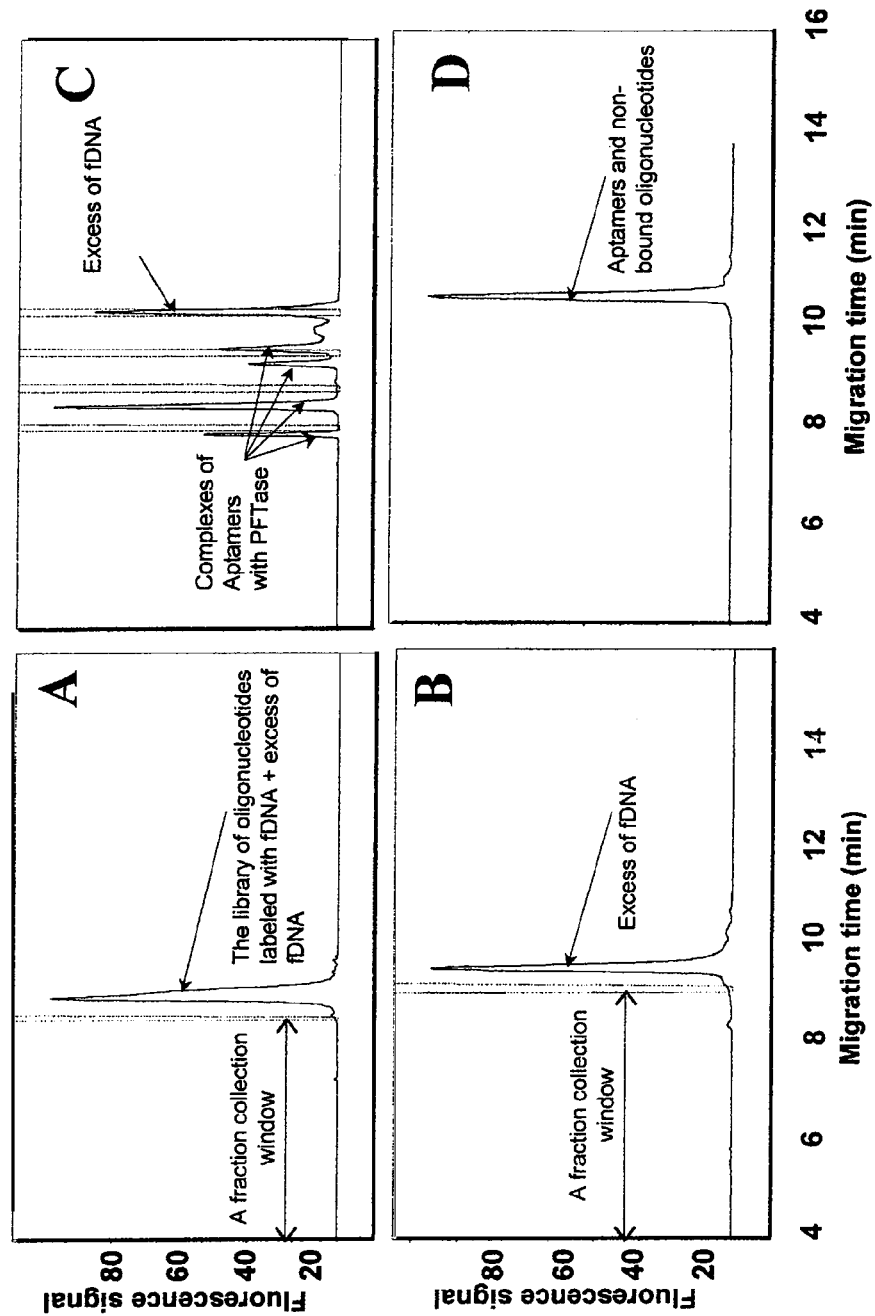
FIG. 15 illustrates the use of a NECEEM-based method for blind selection of oligonucleotide aptamers to PFTase from a combinatorial library of oligonucleotides. Panel A illustrates step 1 in the selection: A fraction from the equilibrium mixture, of the library and PFTase (1 µM), is collected blindly (neither PFTase or the PFTase•aptamer complexes are detectable) from a wide window to the left of the peak of the library. Panel B illustrates step 2 in the selection: A fraction from the equilibrium mixture, of the fraction from step 1, subjected to PCR amplification, and PFTase (1 µM), is collected in a fashion similar to that in step 1. Panel C illustrates the peaks of PFTase•aptamer complexes in the equilibrium mixture, of a PCR-amplified fraction from step 2 and PFTase (1 µM). Two steps of blind selection were sufficient to select aptamers. Panel D illustrates a control electropherogram: A PCR-amplified fraction from step 2 without PFTase.

The migration time of the components of the PFTase sample was determined using UV detection (FIG. 14). This information was used to decide on which side of the sample peak aptamers had to be collected. The peaks of PFTase were not detected during the selection procedure. The conditions of electrophoresis were similar to those described above. The concentration of PFTase was 1 μM. It showed 4 components that could be: PFTase, its 2 subunits, and impurities. All 4 components were targets for selection of aptamers. All 4 components had a migration time shorter than that of the combinatorial library (FIG. 15D). This allowed for the collection of aptamers in the time window to the lets of the peak of the library.

In the first step, the combinatorial library was mixed with the PFTase sample to give a final concentration of 1 μM for the library and 100 nM for the PFTase. The incubation buffer contained 50 mM Tris-HCl at pH 8.3, 10 mM $MgCl_2$, and 10 μM $ZnCl_2$. The equilibration time, $t_{eq}$, was 1000 s. The concentration of PFTase and the equilibration time defined the upper limit of $K_d$ and the lower limit of $k_{on}$ for the aptamers selected: $K_d$<[PFTase]=1 μM and $k_{on}$>1/[PFTase]$t_{eq}$=1×10³ $M^{-1}$ $s^{-1}$. Accordingly, aptamers were selected for $k_{off}$=$K_d k_{on}$≈1×10⁻³ $s^{-1}$. The equilibrium mixture was then injected into the capillary and its components were separated by NECEEM. The fraction from 0 to 8.8 minutes was collected (FIG. 15A) and PCR amplified according to the following protocol. The PCR reaction mixture had a total volume of 100 μL including 10 μL of the fraction collected from NECEEM. The other components of the PCR reaction mixture were: (i) 1 μM of each of two primers to the conserved terminal parts of the oligonucleotides (ii) 10 mM Tris-HCl at pH 8.3, (iii) 50 mM KCl, (iv) 2.5 mM $MgCl_2$, (v) 200 nM of each of the four dNTPs, and (vi) 2.5 units of Taq DNA polymerase. Each PCR cycle consisted of a 30-second denaturation at 94° C., a 30-second annealing at 55° C., and a 30-second extension at 72° C. PCR was performed for 30 cycles using a commercial Master Cycler apparatus (Eppendorf). A biotin moiety was incorporated into the 3' PCR primer which allowed isolation of the nonbiotinylated strand of the PCR products using Affinitip streptavidin coated minicolumns (Hydros). After PCR amplification, ligands were mixed with the PFTase and subjected to an additional round of NECEEM. Two peaks representing complexes of aptamers and two (of the four) components of the PFTase sample were observed after the very first step of selection (FIG. 15B). This equilibrium mixture was subjected to the second round of NECEEM.

Figure 16:
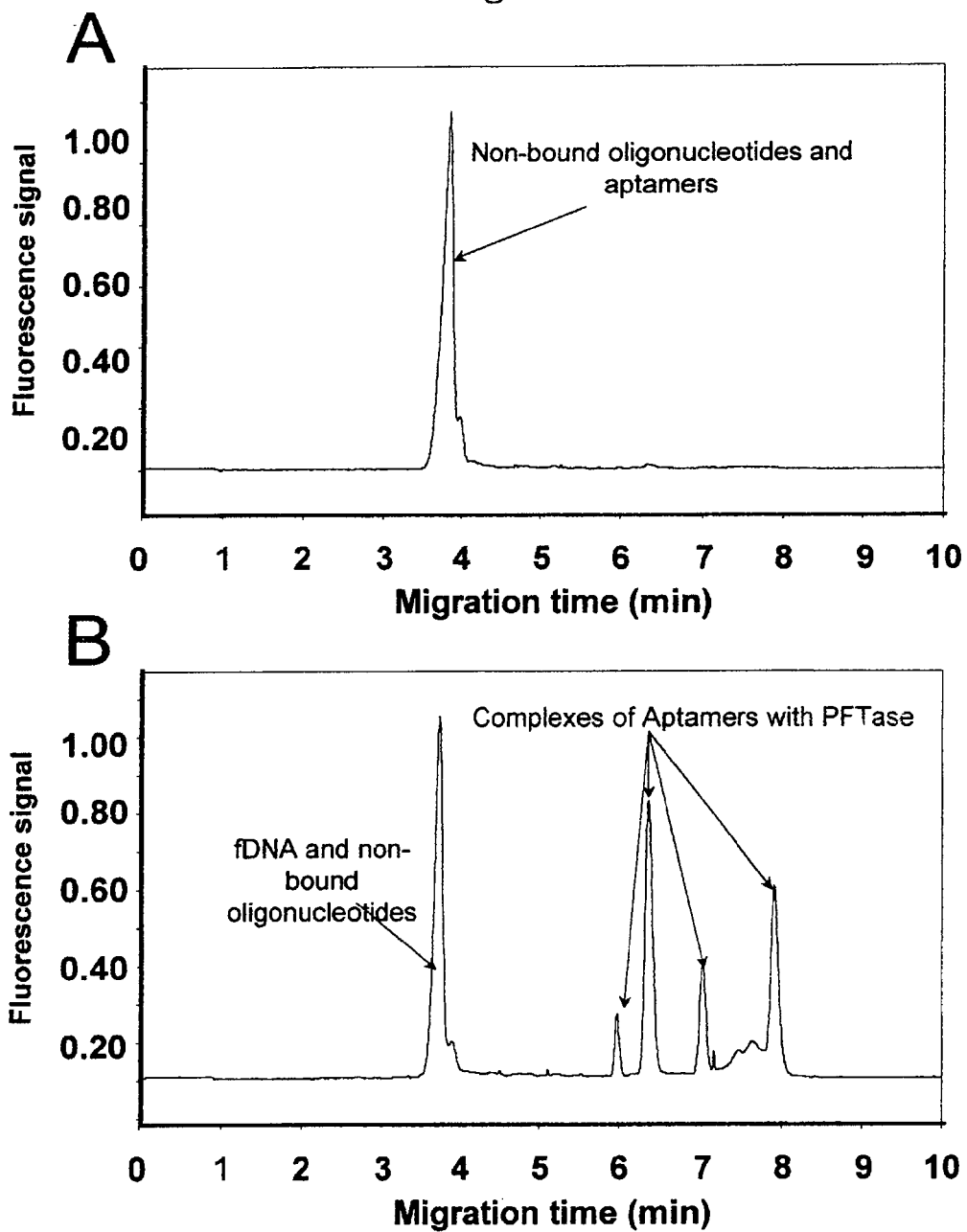
FIG. 16 shows a NECEEM electropherogram of aptamer•PFTase complexes in a buffer that contains 100 nM SSB as a mediator for separating fDNA (used to fluorescently label aptamers and other oligonucleotides of the library) and non-bound oligonucleotides, from the complexes of aptamers and targets. Panel A illustrates an electropherogram of a PCR-amplified fraction from step 2 (see FIG. 15). Panel B shows a NECEEM electropherogram of a PCR-amplified fraction from step 2 with 1 µM PFTase.

In the second round, the pool of aptamers collected in the first iteration, was mixed with the PFTase and subjected to NECEEM. The fraction containing complexes of aptamers with components of the PFTase sample, was collected in the time window between 0 and 8.5 minutes. The collected pool of ligands was PCR amplified as described in the previous paragraph. It was then mixed with the PFTase and subjected to an additional NECEEM. Four peaks corresponding to complexes of aptamers with the four components of the PFTase sample were observed (FIG. 15C). The complexes were collected separately, as shown in FIG. 15C, and PCR amplified. As a result 4 aptamers were obtained for the 4 components of the PFTase sample. The identity of the fDNA peak was confirmed by adding SSB to the NECEEM run buffer. The peak of fDNA moved to shorter migration times while the migration times of the complexes did not change (FIG. 16). This example clearly demonstrates the usefulness of the NECEEM method for the selection of aptamers with specified ranges of binding parameters, the use of the NECEEM method for the selection of aptamers for multiple targets, and the use of SSB as a mediator in the separation of components of an equilibrium mixture subjected to NECEEM.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A homogenous method for determining the kinetic parameters of a complex (L•T) formed between two components (L and T) wherein such parameters are:
   (i) the equilibrium dissociation constant, $K_d$, of said complex
   (ii) the monomolecular rate constant, $k_{off}$, of the decay of said complex
   (iii) the bimolecular rate constant, $k_{on}$, of the formation of said complex wherein the method comprises:
   a) reacting said components under conditions that promote the formation of said complex, and allowing the reaction to come to equilibrium resulting in an equilibrium mixture; wherein said equilibrium mixture can be prepared inside the capillary or outside the capillary, wherein if said equilibrium mixture is prepared outside the capillary a plug of said equilibrium mixture is introduced into the capillary, wherein said capillary is a part of a capillary electrophoresis instrument;
   b) subjecting said equilibrium mixture to capillary electrophoresis under non-equilibrium conditions to permit the decay of said complex and separation of said components and complex;
   c) monitoring the migration of one or more said components and said complex through a detection point on or off the capillary to generate a migration pattern thereof including peaks and curves, the areas under which represent the amounts of said one or more components and/or complex that passed through said detection point;
   d) determining said equilibrium dissociation constant using one of two following equations or their modifications:

$$K_d = \frac{A_L A_T}{A_{LT} + A_{decay}}$$

$$K_d = \frac{[T]_0 \left(1 + \frac{A_L}{A_{LT} + A_{decay}}\right) - [L]_0}{1 + 1 \bigg/ \frac{A_L}{A_{LT} + A_{decay}}}$$

wherein $A_L$, $A_T$, and $A_{L \cdot T}$ are normalized areas of said peaks corresponding to said components L and T and said complex L•T, respectively; $A_{decay}$ is the area under one said curve corresponding to the decay of said complex L•T during said capillary electrophoresis; $[T]_0$ and $[L]_0$ are total concentrations of said components T and L in the equilibrium mixture, respectively; wherein the first equation is applicable to cases when both L and T are detectable and the second equation is applicable to cases when only one said component, L, is detectable;
   e) determining said monomolecular rate constant by fitting one or more said curves of decay of said complex with a single-exponential function:

$$I_t = I_{t_0} \exp\left\{k_{off} \frac{t_{LT}}{t_C - t_{LT}}(t - t_0)\right\}$$

or by:

$$k_{off} = \frac{\ln((A_{LT} + A_{decay})/A_{LT})}{t_{LT}}$$

wherein $t_0$ and $t$ are initial and variable time points on said curve of decay of said complex, $t_C$ is the migration of one of said components, whose signal constitutes said curve, and $t_{L \cdot T}$ is the migration time of said complex in said capillary electrophoresis;
   f) determining said bimolecular rate constant by:

$$k_{on} = k_{off}/K_d.$$

2. The method of claim 1 wherein said components are a protein, peptide, enzyme, nucleic acid, biological sample, aptamer, organelle, cell, virus, particle or other reagent separable by capillary electrophoresis.

3. The method of claim 1 wherein any said component was pretreated by treatments including, lysis, freeze-thaw, centrifugation, enrichment or fractionation.

4. The method of claim 1 wherein one or multiple said components are detected by fluorescence, light absorbance, radioactive, electrochemical, mass or charge detectors, or any combination of them; wherein said components are natively detectable and/or labeled with tags which are detectable by said detectors.

5. The method of claim 1 wherein the parameters of said capillary electrophoresis are optimized by modifications to the voltage, temperature, composition and/or pH of the run buffer, capillary dimensions, the addition of mediators which enhance electrophoretic separation, or capillary pretreatment.

6. The method of claim 1 wherein said kinetic parameters are measured at different temperatures.

7. The method of claim 6 wherein the method is used to determine thermodynamic parameters.

8. The method of claim 7 wherein said thermodynamic parameters are used to measure the temperature in a capillary or other electrophoretic device.

9. A homogeneous method for determining the concentration of a target (T) using an affinity probe (L), comprised of the following steps:
 a) providing an equilibrium mixture of known concentrations of T and L, incubated for time (t) chosen by the operator to reach equilibrium, prepared in a buffer that promotes efficient formation of complex between L and T;
 b) using the method of claim 1 to determine the equilibrium dissociation constant of the formation of the complex L•T;
 c) preparing an equilibrium mixture comprised of unknown concentration of T and known concentration of L; wherein said equilibrium mixture can be prepared inside the capillary or outside the capillary, wherein if said equilibrium mixture is prepared outside the capillary a plug of said equilibrium mixture is introduced into said capillary; wherein said capillary is a part of a capillary electrophoresis instrument;
 d) separating components and complexes by capillary electrophoresis under non-equilibrium conditions optimized by the operator to separate the complex L•T from L;
 e) tracking L and L•T using a detector capable of generating an electropherogram of the migration pattern of the components including peaks and curves;
 f) analyzing peaks and curves to determine the concentration of T using equation:

$$[T]_0 = K_d \Big/ \frac{A_L}{A_{L\cdot T} + A_{decay}} + [L]_0 \Big/ \left(1 + \frac{A_L}{A_{L\cdot T} + A_{decay}}\right)$$

wherein $A_L$ and $A_{L\cdot T}$ are areas of said peaks corresponding to L and L•T, respectively; $A_{decay}$ is the area under one said curve corresponding to the decay of said complex L•T during said capillary electrophoresis; $[T]_0$ and $[L]_0$ are total concentrations of the two components in said equilibrium mixture.

10. The method of claim 9 wherein L and T can be are any of the following: a protein, peptide, enzyme, nucleic acid, aptamer, organelle, cell, virus, combinatorial library, patient sample, biological sample, particle or other reagent separable by capillary electrophoresis.

11. The method of claim 9 wherein L or T or both are pretreated by treatments including but not limited to: purification, lysis, freeze-thaw, centrifugation, enrichment or fractionation.

12. The method of claim 9 wherein the parameters of said capillary electrophoresis are optimized by modifications to the voltage, temperature, composition and/or pH of the run buffer, capillary dimensions, the addition of mediators which enhance electrophoretic separation, or capillary pretreatment.

13. The method of claim 9 wherein the calibration curve is built and used instead of determining and using said equilibrium dissociation constant and said equation.

14. The method of claim 9 wherein T is a protein and L is an aptamer.

15. The method of claim 9 wherein the method is used as a diagnostic tool to measure the concentration of T present in a patient or biological sample.

16. The method of claim 5 wherein the capillary pretreatment is siliconization.

17. The method of claim 10 wherein the combinatorial library comprises peptides, nucleic acids or organic molecules.

18. The method of claim 12 wherein the capillary pretreatment is siliconization.

* * * * *

UNITED STATES PATENT AND TRADEMARK OFFICE
CERTIFICATE OF CORRECTION

PATENT NO. : 8,224,582 B2
APPLICATION NO. : 12/685728
DATED : July 17, 2012
INVENTOR(S) : Sergey N. Krylov et al.

Page 1 of 1

It is certified that error appears in the above-identified patent and that said Letters Patent is hereby corrected as shown below:

On the Title page, item (73) Sergery Krylov, should read --"Sergey Krylov"--.

In the Claims

Column 46, line 4, claim 10 "can be" should read --"are"--.

Signed and Sealed this
Ninth Day of July, 2013

Teresa Stanek Rea
*Acting Director of the United States Patent and Trademark Office*

SEQUENCE LISTING

<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fluorescein-labeled glycine residue

<400> SEQUENCE: 1
gcggagcgtg gcagg                                                        15

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
cctgccacgc tccgctctaa aaataa                                            26

<210> SEQ ID NO 3
<211> LENGTH: 10
<212> TYPE: DNA
<213> ORGANISM: Artificial Sequence
<220> FEATURE:
<223> OTHER INFORMATION: Synthetic

<400> SEQUENCE: 3
ttatttttag                                                              10

<210> SEQ ID NO 4
<211> LENGTH: 71
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(51)
<223> OTHER INFORMATION: n is a, c, g, or t

<400> SEQUENCE: 4
cctgccacgc tccgctnnnn nnnnnnnnnn nnnnnnnnnn nnnnnnnnnn nttcgacatg        60
aggcccggat c                                                            71

<210> SEQ ID NO 5
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Fluoresein-labeled glycine residue

```
<400> SEQUENCE: 5
ttatttttag gcggagcgtg gcagg                                              25

<210> SEQ ID NO 6
<211> LENGTH: 10
<212> TYPE: DNA
<213> ORGANISM: Artificial Sequence
<220> FEATURE:
<223> OTHER INFORMATION: Synthetic

<400> SEQUENCE: 6
gatttttatt                                                               10
```